United States Patent
Giles et al.

(10) Patent No.: US 9,939,408 B2
(45) Date of Patent: Apr. 10, 2018

(54) TRAVELLING WAVE IMS WITH COUNTERFLOW OF GAS

(71) Applicant: Micromass UK Limited, Wilmslow (GB)

(72) Inventors: Kevin Giles, Stockport (GB); Martin Raymond Green, Bowden (GB); David J. Langridge, Macclesfield (GB); Steven Derek Pringle, Hoddlesden (GB); Jason Lee Wildgoose, Stockport (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/107,552

(22) PCT Filed: Dec. 22, 2014

(86) PCT No.: PCT/GB2014/053818
§ 371 (c)(1),
(2) Date: Jun. 23, 2016

(87) PCT Pub. No.: WO2015/097462
PCT Pub. Date: Jul. 2, 2015

(65) Prior Publication Data
US 2016/0320340 A1    Nov. 3, 2016

(30) Foreign Application Priority Data

Dec. 24, 2013 (EP) .................................... 13199573
Dec. 24, 2013 (GB) .................................... 1323004.0

(51) Int. Cl.
*G01N 27/62* (2006.01)
*H01J 49/40* (2006.01)
*H01J 49/42* (2006.01)

(52) U.S. Cl.
CPC ............ *G01N 27/622* (2013.01); *H01J 49/40* (2013.01); *H01J 49/421* (2013.01)

(58) Field of Classification Search
CPC ...... G01N 27/622; H01J 49/40; H01J 49/403; H01J 49/42; H01J 49/421; H01J 49/4255; H01J 49/426; H01J 49/429
See application file for complete search history.

(56) References Cited

U.S. PATENT DOCUMENTS 6,630,662 B1 * 10/2003 Loboda ................ G01N 27/622
250/281
8,253,095 B2    8/2012 Franzen
(Continued)

FOREIGN PATENT DOCUMENTS

GB    2451149    5/2010
GB    2477831    3/2013
(Continued)

Primary Examiner — David E Smith

(57) ABSTRACT

A method of separating ions according to mass to charge ratio is disclosed. The method comprises: providing a separation device comprising a plurality of electrodes; applying one or more transient DC voltages or potentials to at least some of said electrodes in order to urge ions in a first direction through said separation device; and providing a gas flow in a second direction which is substantially inclined or opposed to said first direction. The opposed gas flow unexpectedly improves the mass to charge ratio separation resolution of the device.

20 Claims, 8 Drawing Sheets

(56) References Cited

U.S. PATENT DOCUMENTS

| | | | |
|---|---|---|---|
| 8,263,930 B2* | 9/2012 | Tang | G01N 27/624 |
| | | | 250/282 |
| 8,426,802 B2 | 4/2013 | Giles et al. | |
| 9,070,543 B2 | 6/2015 | Green et al. | |
| 9,244,040 B2 | 1/2016 | Giles et al. | |
| 2009/0302209 A1* | 12/2009 | Green | H01J 49/065 |
| | | | 250/282 |
| 2010/0032561 A1* | 2/2010 | Giles | H01J 49/4235 |
| | | | 250/283 |
| 2010/0108878 A1* | 5/2010 | Bateman | G01N 27/622 |
| | | | 250/283 |
| 2011/0095175 A1 | 4/2011 | Bateman | |

FOREIGN PATENT DOCUMENTS

| | | |
|---|---|---|
| GB | 2486584 | 7/2014 |
| WO | 1999/021212 | 11/2001 |
| WO | 2007/125354 | 11/2007 |

* cited by examiner

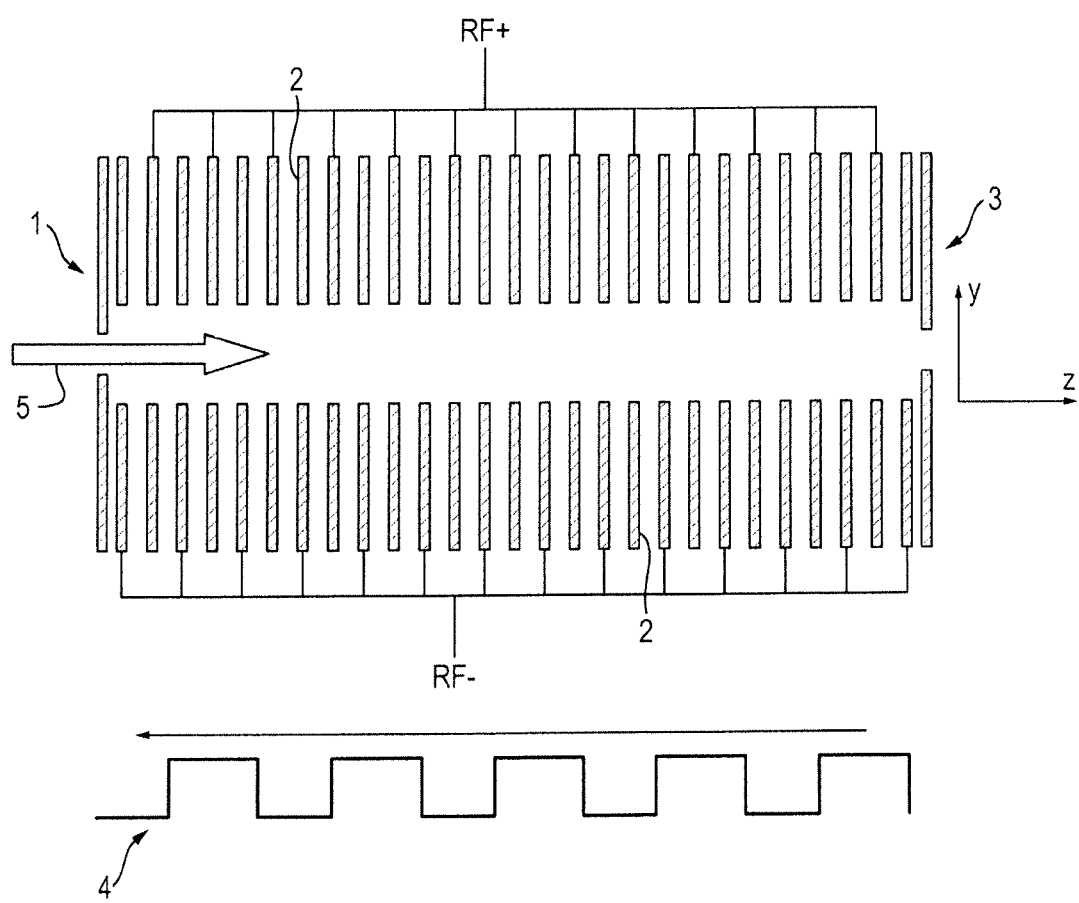

TRAVELLING WAVE IMS WITH COUNTERFLOW OF GAS

CROSS REFERENCE TO RELATED APPLICATIONS

This application is the National Stage of International Application No. PCT/GB2014/053818, filed 22 Dec. 2014 which claims priority from and the benefit of United Kingdom patent application No. 1323004.0 filed on 24 Dec. 2013 and European patent application No. 13199573.0 filed on 24 Dec. 2013. The entire content of these applications are incorporated herein by reference.

BACKGROUND TO THE PRESENT INVENTION

The present invention relates to an ion separation device.

Ion mobility spectrometers or separators are well known. One particular known ion mobility separator is described with reference to FIG. 7 of U.S. Pat. No. 6,630,662 (Loboda). The known ion mobility separator comprises a segmented quadrupole rod set ion mobility separator. An axial DC voltage gradient is maintained along the length of the ion mobility separator and a counterflow of gas is provided.

One problem with the known arrangement is that the ion mobility separator is essentially equivalent to a conventional ion mobility separator having a longer drift length. Although the arrangement disclosed in US-6630662 enables a more compact ion mobility separator to be provided it does not offer any other improvement.

It is desired to provide an improved method of separating ions and separation device.

SUMMARY OF THE PRESENT INVENTION

According to a first aspect the present invention provides a method of separating ions comprising:

providing a separation device comprising a plurality of electrodes;

applying one or more transient DC voltages or potentials to at least some of said electrodes in order to urge ions in a first direction through said separation device;

providing a gas flow in a second direction which is substantially inclined or opposed to said first direction;

performing a first mode of operation in which said one or more transient DC voltages are swept, translated or sequentially applied along at least a portion of the axial length of said separation device with a first velocity so as to cause ions to be separated according to their ion mobilities; and performing a second mode of operation in which said one or more transient DC voltages are swept, translated or sequentially applied along at least a portion of the axial length of said separation device with a second velocity that is higher than said first velocity so as to cause ions to be separated according to their mass to charge ratios;

wherein said gas flow is provided during said first and second modes.

A particular advantage of the separation device according to the present invention is that the separation device provides improved functionality compared with conventional ion mobility separators such as the ion mobility separator disclosed in US-6630662.

The present invention is particularly advantageous in that the preferred ion separator has improved ion mobility separation and mass to charge ratio separation, and can easily be switched between different modes of operation. In one mode of operation ions are separated according to their ion mobility (or collision cross section) and in another mode of operation ions are separated according to their mass or mass to charge ratio. This is not possible with the arrangement disclosed in US-6630662.

As will be understood by those skilled in the art, conventional ion mobility separators utilising a DC drift tube cannot be operated in a mode of operation wherein separation is predominantly related to mass or mass to charge ratio, as the separation mechanism is fundamentally different compared to travelling wave ion mobility separators (i.e. devices wherein one or more transient DC voltages or potentials are applied to the electrodes forming the ion mobility separator).

A counterflow of gas is used to provide an ion mobility separator or filter and a mass or mass to charge ratio separator or filter which is able to separate ions temporally, preferably from a continuous ion beam.

The use of a counter gas flow to improve mass to charge ratio resolution is counter-intuitive in that mass to charge ratio separation is generally desired to be performed at low pressures, whereas the use of a counter gas flow has conventionally been seen as having the effect of increasing the pressure in the device.

The preferred separation device preferably comprises an RF confined ion guide. Ions are urged along and through the axial length of the ion guide by applying a travelling wave or one or more transient DC potentials or voltages to the electrodes comprising the ion guide. The ion guide is supplied with a buffer gas (e.g. helium or nitrogen) such that ions received into the ion guide and onwardly transmitted by the ion guide separate in time according to their ion mobility or collision cross section during transit through the ion guide. The buffer gas is supplied or caused to flow in an opposed or inclined direction to the direction that the travelling wave or one or more transient DC voltages or potentials are applied to the electrodes and the direction that an axial DC potential barrier is translated along the length of the ion guide. For example, according to an embodiment one or more transient DC voltages or potentials may be progressively applied to the electrodes so that an axial DC potential barrier moves from an entrance of the device to an exit of the device and at the same time a buffer gas is preferably arranged to flow from the exit of the device towards the entrance of the device i.e. in an opposed direction to the direction of travel of the transient DC voltages or potentials applied to the electrodes.

In an ion mobility separator which utilises a travelling wave or one or more transient DC voltages or potentials in order to urge ions along the axial length of the device it will be understood that ions do not experience a continuous force driving the ions towards the exit of the device. Ions are overtaken by the travelling wave or transient DC voltage or potential barriers as the ions become temporally separated and hence experience a driving force towards the exit for only a portion of the time in which the ions take to traverse the device. For the remainder of the time the ions experience either zero force or a net force which drives the ions back towards the entrance of the device.

It will therefore be appreciated by those skilled in the art that the nature of ion mobility separation which is utilised by a travelling wave ion mobility separator according to the preferred embodiment is quite different to the mechanism which separates ions in a conventional ion mobility separator. As will be understood by those skilled in the art a conventional ion mobility separator utilises a drift cell in combination with a static DC field which is maintained along the axial length of the ion mobility separator.

The different nature of the ion mobility separation utilising a travelling wave ion mobility separator is fundamental to the operation of a travelling wave separator. When the ion mobility separator is operated so that travelling waves or transient DC voltages or potentials are translated along the length of the device at relatively low speeds then ions reach a terminal velocity and are separated temporally predominately according to their ion mobility or collision cross section.

Applying a counterflow of gas in a direction which is substantially opposed to the direction in which the travelling wave propagates along the length of the ion mobility separator increases the ion mobility separation power and extends the ion mobility drift time. Furthermore, the ion mobility separator can be easily adjusted in order to change the mechanism by which ions are temporally separated, i.e. the device can be easily controlled to separate ions according to their ion mobility or collision cross section and then adjusted so as to separate ions according to their mass or mass to charge ratio.

When a counterflow of gas is applied to the ion mobility separator, for a given wave amplitude and velocity, the drift time is extended because an ion having a particular ion mobility or collision cross section will be overtaken by the travelling wave or transient DC voltages or potentials as they are sequentially applied to adjacent electrodes more times during its drift time. The same effect may be accomplished by increasing the travelling wave velocity or reducing the time between applying transient DC voltages or potentials to neighbouring electrodes.

Intuitively this could be considered to be equivalent to applying a counterflow of gas as the drift time for an ion of given mobility is increased and hence the number of times the ion is overtaken by the travelling wave or transient DC voltages or potentials is increased. However, in contrast to applying a counterflow of gas, the act of increasing the travelling wave velocity does not actually result in a significant increase in the ion mobility separation power or ion mobility resolution of the system. Indeed, when the speed of the travelling wave or transient DC voltages or potentials is significantly increased then the device begins to separate ions predominantly according to their mass or mass to charge ratio rather than according to their ion mobility.

Applying a counterflow of gas in conjunction with a travelling wave ion mobility separator has several advantages over conventional arrangements including conventional arrangements utilising a counterflow of gas.

The resolution of conventional ion mobility separators which urge ions along the length of the ion mobility separator against a static buffer gas depends upon the square root of the electric field which is applied along the axial length of the ion mobility separator and upon the square root of the length of the device.

For conventional ion mobility separation devices using static DC fields, in order to maintain the electric field over longer ion mobility separation cells, the potential drop over the ion mobility separation device becomes relatively large and eventually impractical due to discharge. In contrast, travelling wave ion mobility separators according to the preferred embodiment do not suffer from this limitation and furthermore the amplitude of the transient DC voltage or potential which is preferably applied to the electrodes may be relatively low and the amplitude of the transient DC voltage or potential is preferably independent of the length of the device.

One advantageous aspect of the present invention is that a high resolution extended ion mobility separation device is preferably provided which may be operated using relatively low amplitude transient DC voltages. The amplitude of the transient DC voltages or potentials applied to the electrodes is relatively low compared to conventional devices which utilise an axial DC driving force.

Also, increasing the velocity of the travelling wave or the rate at which the transient DC voltages or potentials are applied along the length of the device can result in separation which is highly correlated to mass to charge ratio rather than separation dominated by ion mobility or collision cross section.

In the preferred mode of operation wherein ions are separated according to their ion mobility or collision cross section the ions do not reach terminal velocity as they are accelerated by the travelling wave potential or the transient DC voltages or potentials. Once ions are overtaken by the travelling wave or the transient DC voltages or potentials as they are being translated along the length of the device the ions then lose most or all of their forward velocity. On average the forward velocity of the ions is related to the mass to charge ratio. This results in the drift time of the ions being much more strongly correlated with the mass to charge ratio of the ions rather than the ion mobility or collision cross section of the ions.

The switch from ion mobility separation to mass to charge ratio separation by increasing the speed of the travelling wave is a unique attribute of travelling wave ion mobility separations and cannot be reproduced using conventional ion mobility separators which utilise a static DC field in combination with a conventional drift tube.

As a result, the ion separation device according to the present invention enables the same device to be used to separate ions based predominantly upon their ion mobility or collision cross section or alternatively based to a larger extent upon their mass to charge ratio simply by changing the operational parameters of the travelling wave or the transient DC voltages or potentials applied to the electrodes.

This characteristic can be useful if the separation device is to be used as part of a linked scan to improve the duty cycle of a scanning mass to charge ratio filter such as a quadrupole mass filter.

Switching between ion mobility or collision cross section separation and mass to charge ratio separation may be achieved by altering the travelling wave parameters.

Preferably, said second mode causes ions to exit the separation device in order of increasing or decreasing mass to charge ratio; wherein the second mode further comprises: transmitting the ions, whilst separated, from the separation device to a downstream ion analyser; and varying the operation of the ion analyser as a function of time, based on and in synchronism with the mass to charge ratios of the ions exiting the separation device and being received at the ion analyser.

This second mode may be advantageous, for example, in that it enables the duty cycle of the ion analyser to be optimised or improved.

The ion analyser may comprise an ion filter that only transmits ions having a certain value or range of values of a physicochemical property at any given time during, and the value or range of values transmitted by the ion filter may be varied with time in said second mode based on and in synchronism with the mass to charge ratios of the ions exiting the separation device and being received at the ion analyser.

The ions transmitted by the ion filter may be detected, such that the physicochemical property values of any detected ions can be determined from knowledge of the physicochemical property values being transmitted by the filter at the time of detection.

The ion filter may be a quadrupole, or other multipole, mass filter.

Alternatively, the ion analyser may be a discontinuous ion analyser that receives ions from the separation device and repeatedly pulses ions into an analysis region. The duration of time between the pulses may be varied as a function of time, based on and in synchronism with the mass to charge ratios of the ions exiting the separation device and being received at the ion analyser. Alternatively, the duration of time between any given ion exiting the separation device and being pulsed into the analysis region is varied as a function of time, based on and in synchronism with the mass to charge ratios of the ions exiting the separation device and being received at the ion analyser.

Accordingly, the length of time between ions of a first mass to charge ratio (or first range of mass to charge ratios) exiting the separation device and being pulsed into the analysis region may be different to the length of time between ions of a second mass to charge ratio (or second range of mass to charge ratios) exiting the separation device and being pulsed into the analysis region. This may enable the pulsed extraction region of the ion analyser to be filled with ions more efficiently and hence may improve the duty cycle of the ion analyser.

The ion analyser may be a Time of Flight mass analyser and the analysis region may be a Time of Flight region.

The ion analyser described herein may be a mass analyser and/or the physicochemical property may be mass to charge ratio.

Said first mode may cause ions to exit the separation device in order of increasing or decreasing ion mobility; and the first mode may further comprise: transmitting the ions, whilst separated, from the separation device to a downstream ion analyser; and varying the operation of the ion analyser as a function of time, based on and in synchronism with the ion mobilities of the ions exiting the separation device and being received at the ion analyser.

In the first mode, the ion analyser may comprise an ion filter that only transmits ions having a certain value or range of values of a physicochemical property at any given time, and the value or range of values transmitted by the ion filter may be varied with time in said first mode based on and in synchronism with the ion mobilities of the ions exiting the separation device and being received at the ion analyser.

The ions transmitted by the ion filter may be detected, such that the physicochemical property values of any detected ions can be determined from knowledge of the physicochemical property values being transmitted by the filter at the time of detection.

The ion filter may be a quadrupole, or other multipole, mass filter.

The ion analyser operating in the first mode may be a mass analyser and/or the physicochemical property may be mass to charge ratio.

The mass to charge ratio(s) of the ions transmitted by the ion filter in said first mode may be varied with time and as a function of the ion mobilities received at the ion filter from the separation device so as to only transmit ions of a selected charge state.

The ion analyser may be a discontinuous ion analyser that receives ions from the separation device in the first mode and repeatedly pulses ions into an analysis region; wherein the duration of time between the pulses is varied as a function of time, based on and in synchronism with the ion mobilities of the ions exiting the separation device and being received at the ion analyser; or wherein the duration of time between any given ion exiting the separation device and being pulsed into the analysis region is varied as a function of time, based on and in synchronism with the ion mobilities of the ions exiting the separation device and being received at the ion analyser. Accordingly, the length of time between ions of a first ion mobility (or first range of ion mobilities) exiting the separation device and being pulsed into the analysis region may be different to the length of time between ions of a second ion mobility (or second range of ion mobilities) exiting the separation device and being pulsed into the analysis region.

The discontinuous ion analyser may be a mass analyser.

The ion analyser may be a Time of Flight mass analyser and the analysis region may be a Time of Flight region.

The method may comprise determining the mass to charge ratios of the separated ions in the second mode.

The separation device may comprise or form part of a flight region, and said second mode may comprise urging the ions through the flight region in the first direction using the one or more transient DC voltages or potentials, determining the times of flight of the ions through the flight region, and determining the mass to charge ratios of the ions from the times of flight of the ions through the flight region.

The step of determining the mass to charge ratios of the ions may comprise detecting the ions exiting the flight region.

The gas flows through the time of flight region in the second direction.

The method may comprise measuring the ion mobilities of the separated ions in the first mode.

The separation device may comprise or form part of a flight region, and said first mode may comprise urging the ions through the flight region in the first direction using the one or more transient DC voltages or potentials, determining the times of flight of the ions through the flight region, and determining the ion mobilities of the ions from the times of flight of the ions through the flight region.

The step of determining the ion mobilities of the ions may comprise detecting the ions exiting the flight region.

The gas flows through the time of flight region in the second direction.

Ions having the same mass to charge ratio but differing ion mobilities are preferably separated in the first mode; and/or ions having the same ion mobility but differing mass to charge ratios are preferably separated in the second mode.

The method preferably separates the ions with a higher ion mobility resolution in the first mode than in the second mode; and/or the method preferably separates the ions with a higher mass to charge ratio resolution in the second mode than in the first mode.

Ions are predominantly separated by ion mobility in the first mode and predominately separated by mass to charge ratio in the second mode.

Preferably, the one or more transient DC voltages or potentials are repeatedly swept or traveled along the device during said first mode so as to urge the ions in the first direction. Preferably, the one or more transient DC voltages or potentials are repeatedly swept or traveled along the device during said second mode so as to urge the ions in the first direction.

The velocity of the one or more transient DC voltages in the first mode may be ≤x % of the velocity of the one or more transient DC voltages in the second mode, wherein x is selected from the group consisting of: 90; 80; 70; 60; 50; 40; 30; 20; 10; or 5.

In the first mode, the one or more DC voltage or potential barriers and counter gas flow preferably cause the ions to reach their terminal velocities; and in second mode the one or more DC voltage or potential barriers and counter gas flow preferably do not cause the ions to reach their terminal velocities.

The first velocity may be selected from the group consisting of: (i) <100 m/s; (ii) 100-200 m/s; (iii) 200-300 m/s; (iv) 300-400 m/s; (v) 400-500 m/s; (vi) 500-600 m/s; (vii) 600-700 m/s; (viii) 700-800 m/s; (ix) 800-900 m/s; (x) 900-1000 m/s; (xi) 1000-1100 m/s; (xii) 1100-1200 m/s; (xiii) 1200-1300 m/s; (xiv) 1300-1400 m/s; (xv) 1400-1500 m/s; (xvi) 1500-1600 m/s; (xvii) 1600-1700 m/s; (xviii) 1700-1800 m/s; (xix) 1800-1900 m/s; (xx) 1900-2000 m/s; (xxi) 2000-2100 m/s; (xi) (xxii) 2100-2200 m/s; (xxiii) 2200-2300 m/s; (xxiv) 2300-2400 m/s; (xxv) 2400-2500 m/s; (xxvi) 2500-2600 m/s; (xxvii) 2600-2700 m/s; (xxviii) 2700-2800 m/s; (xxix) 2800-2900 m/s; (xxx) 2900-3000 m/s; and (xxxi)>3000 m/s.

Preferably, the first velocity is less than 1000 m/s. The second velocity may be selected from the group consisting of: (i) <100 m/s; (ii) 100-200 m/s; (iii) 200-300 m/s; (iv) 300-400 m/s; (v) 400-500 m/s; (vi) 500-600 m/s; (vii) 600-700 m/s; (viii) 700-800 m/s; (ix) 800-900 m/s; (x) 900-1000 m/s; (xi) 1000-1100 m/s; (xii) 1100-1200 m/s; (xiii) 1200-1300 m/s; (xiv) 1300-1400 m/s; (xv) 1400-1500 m/s; (xvi) 1500-1600 m/s; (xvii) 1600-1700 m/s; (xviii) 1700-1800 m/s; (xix) 1800-1900 m/s; (xx) 1900-2000 m/s; (xxi) 2000-2100 m/s; (xi) (xxii) 2100-2200 m/s; (xxiii) 2200-2300 m/s; (xxiv) 2300-2400 m/s; (xxv) 2400-2500 m/s; (xxvi) 2500-2600 m/s; (xxvii) 2600-2700 m/s; (xxviii) 2700-2800 m/s; (xxix) 2800-2900 m/s; (xxx) 2900-3000 m/s; and (xxxi)>3000 m/s.

Preferably, the second velocity is more than 1000 m/s.

The method may comprise varying, scanning or stepping the amplitude of said one or more transient DC voltages or potentials as a function of time during said first mode and/or second mode; and/or wherein said one or more transient DC voltages or potentials may have different amplitudes during said first and second modes.

The method may comprise increasing and/or decreasing the amplitude of said one or more transient DC voltages or potentials as a function of time during said first mode and/or second mode; and/or wherein said one or more transient DC voltages or potentials may have a higher amplitude during said first mode than the second mode, or a lower amplitude during said first mode than the second mode.

It will be appreciated that said step of separating ions by their ion mobility in the first mode may comprise separating ions according to their collision cross section ("CCS") or differential ion mobility.

In said first and/or second mode of operation, ions may be separated in a separation region maintained at a pressure selected from the group consisting of: (i)<0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; (ix)>1000 mbar; (x) ≤5 mbar; and (xi) <10 mbar.

Pressures of ≤5 mbar or ≤10 mbar are particularly advantageous in the second mode of operation. More specifically, it has been found desirable to maintain gas pressures at or below these values during the mass to charge ratio separation mode and to apply a counter gas flow to improve separation, rather than increasing gas pressure.

The gas flow may have a velocity in said second direction selected from the group consisting of: (i) <10 m/s; (ii) 10-20 m/s; (iii) 20-30 m/s; (iv) 30-40 m/s; (v) 40-50 m/s; (vi) 50-60 m/s; (vii) 60-70 m/s; (viii) 70-80 m/s; (ix) 80-90 m/s; (x) 90-100 m/s; and (xi) >100 m/s.

Ions may enter a separation region, be separated in said first and second modes according to ion mobility or mass to charge ratio, and then exit the separation region; wherein said first direction is either: (i) from an ion exit end of said separation region towards an ion entrance end of said separation region; or (ii) from an ion entrance end of said separation region towards an ion exit end of said separation region.

Ions may be arranged to progressively exit from or elute from the separation device over a period of time either: (i) substantially in order of their ion mobility, collision cross section or differential ion mobility during the first mode; (ii) substantially in reverse order of their ion mobility, collision cross section or differential ion mobility during the first mode; (iii) substantially in order of their mass, mass to charge ratio or time of flight during the second mode; or (ii) substantially in reverse order of their mass, mass to charge ratio or time of flight during the second mode.

The method may switch between said first and second modes, preferably whilst analysing the same sample in a single experimental run.

The force for driving ions in the first direction may be provided by a multiphase AC or RF voltage being applied to the electrodes, rather than one or more transient DC voltages or potentials.

Accordingly, from a second aspect the present invention provides a method of separating ions comprising:

providing a separation device comprising a plurality of electrodes;

applying multi-phase AC or RF voltages or potentials to at least some of said electrodes, switching the phase of the voltages or potentials applied to sequential electrodes along the device such that a pseudo-potential barrier moves along the device or modulating the amplitude of the voltages or potentials in sequence along the device such that a pseudo-potential barrier moves along the device, wherein the potential barrier urges ions in a first direction through said separation device; and providing a gas flow in a second direction which is substantially inclined or opposed to said first direction;

performing a first mode of operation in which said one or more AC or RF voltages or potentials are applied along at least a portion of the axial length of said separation device so that said potential barrier moves along the device at a first velocity so as to cause ions to be separated according to their ion mobilities; and performing a second mode of operation in which said one or more AC or RF voltages or potentials are applied along at least a portion of the axial length of said separation device so that said potential barrier moves along the device at a second velocity that is higher than said first velocity so as to cause ions to be separated according to their mass to charge ratios;

wherein said gas flow is provided during said first and second modes.

The electrodes to which the various phases of the multi-phase AC or RF voltages or potentials are applied are selected such that the ions are urged in the first direction.

The multi-phase AC or RF voltages or potentials preferably comprises a 3-phase, 4-phase, 5-phase, 6-phase, 7-phase, 8-phase, 9-phase or 10-phase AC or RF voltage supply to act as an RF drive. According to other embodiments the AC or RF voltage supply may comprise more than ten phases.

The method according to the second aspect may comprise any of the preferred or optional features discussed in relation to the first aspect, except wherein the ions are driven in the first direction by the multi-phase AC or RF voltages or potentials, rather than by the one or more DC voltage or potential barriers.

The method may comprise varying, scanning or stepping the amplitude of said multi-phase AC or RF voltages as a function of time during said first mode and/or second mode; and/or wherein said multi-phase AC or RF voltages may have different amplitudes during said first and second modes.

The method may comprise increasing and/or decreasing the amplitude of said multi-phase AC or RF voltages as a function of time during said first mode and/or second mode; and/or wherein said multi-phase AC or RF voltages may have a higher amplitude during said first mode than the second mode, or a lower amplitude during said first mode than the second mode.

The concept of using one or more transient DC voltages or potentials and a counter gas flow to improve mass to charge ratio separation is believed to be novel in its own right.

Accordingly, from a third aspect the present invention provides a method of separating ions according to mass to charge ratio, comprising:

providing a separation device comprising a plurality of electrodes;

applying one or more transient DC voltages or potentials to at least some of said electrodes in order to urge ions in a first direction through said separation device; and providing a gas flow in a second direction which is substantially inclined or opposed to said first direction.

Preferably, ions are caused to exit the separation device in order of increasing or decreasing mass to charge ratio; wherein the method further comprises: transmitting the ions, whilst separated, from the separation device to a downstream ion analyser; and varying the operation of the ion analyser as a function of time, based on and in synchronism with the mass to charge ratios of the ions exiting the separation device and being received at the ion analyser.

This mode may be advantageous, for example, in that it enables the duty cycle of the ion analyser to be optimised or improved.

The ion analyser may comprise an ion filter that only transmits ions having a certain value or range of values of a physicochemical property at any given time during, and the value or range of values transmitted by the ion filter may be varied with time based on and in synchronism with the mass to charge ratios of the ions exiting the separation device and being received at the ion analyser.

The ions transmitted by the ion filter may be detected, such that the physicochemical property values of any detected ions can be determined from knowledge of the physicochemical property values being transmitted by the filter at the time of detection.

The ion filter may be a quadrupole, or other multipole, mass filter.

Alternatively, the ion analyser may be a discontinuous ion analyser that receives ions from the separation device and repeatedly pulses ions into an analysis region; and wherein the duration of time between the pulses is varied as a function of time, based on and in synchronism with the mass to charge ratios of the ions exiting the separation device and being received at the ion analyser; or wherein the duration of time between any given ion exiting the separation device and being pulsed into the analysis region is varied as a function of time, based on and in synchronism with the mass to charge ratios of the ions exiting the separation device and being received at the ion analyser.

Accordingly, the length of time between ions of a first mass to charge ratio (or first range of mass to charge ratios) exiting the separation device and being pulsed into the analysis region may be different to the length of time between ions of a second mass to charge ratio (or second range of mass to charge ratios) exiting the separation device and being pulsed into the analysis region. This may enable the pulsed extraction region of the ion analyser to be filled with ions more efficiently and hence may improve the duty cycle of the ion analyser.

The ion analyser may be a Time of Flight mass analyser and the analysis region may be a Time of Flight region.

The ion analyser described herein may be a mass analyser and/or the physicochemical property may be mass to charge ratio.

The preferably comprises determining the mass to charge ratios of the separated ions.

The separation device may comprise or forms part of a flight region, and the method may comprise urging the ions through the flight region in the first direction using the one or more transient DC voltages or potentials, determining the times of flight of the ions through the flight region, and determining the mass to charge ratios of the ions from the times of flight of the ions through the flight region.

The step of determining the mass to charge ratios of the ions may comprise detecting the ions exiting the flight region.

The gas flows through the time of flight region in the second direction.

Preferably, ions having the same mass to charge ratio but differing ion mobilities are separated by the device.

Preferably, the one or more DC voltage or potential barriers and the counter gas flow do not result in the ions reaching their terminal velocities as they pass through the device.

The one or more transient DC voltages or potentials are applied to at least some of said electrodes so that said one or more DC voltage or potential barriers are preferably swept, translated or sequentially applied along at least a portion of the axial length of said separation device with a first velocity.

Preferably, the one or more transient DC voltages or potentials are repeatedly swept or traveled along the device so as to urge the ions in the first direction.

The method may comprise varying, scanning or stepping the velocity of said one or more transient DC voltages or potentials in said first direction as a function of time.

Preferably, the ions are separated with higher mass to charge ratio resolution when the one or more transient DC voltages or potentials have a higher velocity, and a lower mass to charge ratio resolution when the one or more transient DC voltages or potentials have a lower velocity.

The velocity of said one or more transient DC voltages or potentials may be selected from the group consisting of: (i) <100 m/s; (ii) 100-200 m/s; (iii) 200-300 m/s; (iv) 300-400 m/s; (v) 400-500 m/s; (vi) 500-600 m/s; (vii) 600-700 m/s; (viii) 700-800 m/s; (ix) 800-900 m/s; (x) 900-1000 m/s; (xi) 1000-1100 m/s; (xii) 1100-1200 m/s; (xiii) 1200-1300 m/s; (xiv) 1300-1400 m/s; (xv) 1400-1500 m/s; (xvi) 1500-1600 m/s; (xvii) 1600-1700 m/s; (xviii) 1700-1800 m/s; (xix) 1800-1900 m/s; (xx) 1900-2000 m/s; (xxi) 2000-2100 m/s;

(xi) (xxii) 2100-2200 m/s; (xxiii) 2200-2300 m/s; (xxiv) 2300-2400 m/s; (xxv) 2400-2500 m/s; (xxvi) 2500-2600 m/s; (xxvii) 2600-2700 m/s; (xxviii) 2700-2800 m/s; (xxix) 2800-2900 m/s; (xxx) 2900-3000 m/s; and (xxxi)>3000 m/s. Preferably, the velocity is >1000 m/s.

The method may comprise varying, scanning or stepping the amplitude of said one or more transient DC voltages or potentials as a function of time.

The method may comprise increasing and/or decreasing the amplitude of said one or more transient DC voltages or potentials as a function of time.

The separation device may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix)>1000 mbar.

Preferably, the pressure is 5 mbar or 10 mbar.

The gas flow may have a velocity in said second direction selected from the group consisting of: (i) <10 m/s; (ii) 10-20 m/s; (iii) 20-30 m/s; (iv) 30-40 m/s; (v) 40-50 m/s; (vi) 50-60 m/s; (vii) 60-70 m/s; (viii) 70-80 m/s; (ix) 80-90 m/s; (x) 90-100 m/s; and (xi) >100 m/s.

The first direction may be either: (i) from an ion exit end of said separation device towards an ion entrance end of said separation device; or (ii) from an ion entrance end of said separation device towards an ion exit end of said separation device.

Ions may be arranged to progressively exit from or elute from said separation device over a period of time either: (i) substantially in order of their mass, mass to charge ratio or time of flight; or (ii) substantially in reverse order of their mass, mass to charge ratio or time of flight.

The force for driving ions in the first direction may be provided by a multi-phase AC or RF voltage being applied to the electrodes, rather than one or more transient DC voltages or potentials.

Accordingly, from a fourth aspect the present invention provides a method of separating ions according to mass to charge ratio or ion mobility, comprising:

providing a separation device comprising a plurality of electrodes;

applying multi-phase AC or RF voltages or potentials to at least some of said electrodes, switching the phase of the voltages or potentials applied to sequential electrodes along the device such that a pseudo-potential barrier moves along the device or modulating the amplitude of the voltages or potentials in sequence along the device such that a pseudo-potential barrier moves along the device, wherein the potential barrier urges ions in a first direction through said separation device; and providing a gas flow in a second direction which is substantially inclined or opposed to said first direction.

The electrodes to which the various phases of the multi-phase AC or RF voltages or potentials are applied are selected such that the ions are urged in the first direction.

The multi-phase AC or RF voltages or potentials preferably comprises a 3-phase, 4-phase, 5-phase, 6-phase, 7-phase, 8-phase, 9-phase or 10-phase AC or RF voltage supply to act as an RF drive. According to other embodiments the AC or RF voltage supply may comprise more than ten phases.

The method according to the fourth aspect may comprise any of the preferred or optional features discussed in relation to the third aspect, except wherein the ions are driven in the first direction by the multi-phase AC or RF voltages or potentials, rather than by the one or more DC voltage or potential barriers.

The method may comprise increasing and/or decreasing the amplitude of said multi-phase AC or RF voltages as a function of time.

The present invention also provides a method of mass spectrometry or ion mobility spectrometry comprising a method as described herein.

The present invention also provides a separation device for performing the methods described herein.

Accordingly, from the first aspect the present invention provides a separation device for separating ions, comprising:

a plurality of electrodes;

a first device arranged and adapted to apply one or more transient DC voltages or potentials to at least some of said electrodes in order to urge ions in a first direction through said separation device;

a second device arranged and adapted to provide a gas flow in a second direction which is substantially inclined or opposed to said first direction;

a controller arranged and adapted to control the first and second devices to:

perform a first mode of operation in which said one or more transient DC voltages are swept, translated or sequentially applied along at least a portion of the axial length of said separation device with a first velocity so as to cause ions to be separated according to their ion mobilities;

perform a second mode of operation in which said one or more transient DC voltages are swept, translated or sequentially applied along at least a portion of the axial length of said separation device with a second velocity that is higher than said first velocity so as to cause ions to be separated according to their mass to charge ratios; and provide said gas flow during said first and second modes.

The device may be arranged and configured to perform any one of the preferred or optional methods described in relation to the first aspect of the present invention.

From the second aspect the present invention provides a separation device for separating ions, comprising:

a plurality of electrodes;

a first device arranged and adapted to apply multi-phase AC or RF voltages or potentials to at least some of said electrodes and to switch the phase of the voltages or potentials applied to sequential electrodes along the device such that a pseudo-potential barrier moves along the device or to modulate the amplitude of the voltages or potentials in sequence along the device such that a pseudo-potential barrier moves along the device, wherein the potential barrier is configured to urge ions in a first direction through said separation device;

a second device arranged and adapted to provide a gas flow in a second direction which is substantially inclined or opposed to said first direction;

a controller arranged and adapted to control the first and second devices to:

perform a first mode of operation in which said one or more AC or RF voltages or potentials are applied along at least a portion of the axial length of said separation device so that said potential barrier moves along the device at a first velocity so as to cause ions to be separated according to their ion mobilities;

perform a second mode of operation in which said one or more AC or RF voltages or potentials are applied along at least a portion of the axial length of said separation device so that said potential barrier moves along the device at a second velocity that is higher than said first velocity so as to cause ions to be separated according to their mass to charge ratios; and provide said gas flow during said first and second modes.

From the third aspect the present invention provides a separation device for separating ions according to mass to charge ratio, comprising:

a plurality of electrodes;

a first device arranged and adapted to apply one or more transient DC voltages or potentials to at least some of said electrodes in order to urge ions in a first direction through said separation device; and a second device arranged and adapted to provide a gas flow in a second direction which is substantially inclined or opposed to said first direction; and a controller arranged and adapted to control the first and second devices so that the one or more transient DC voltages or potentials urge the ions against the gas flow such that the ions separate according to their mass to charge ratios.

From the fourth aspect the present invention provides a separation device for separating ions according to mass to charge ratio or ion mobility, comprising:

a plurality of electrodes;

a first device arranged and adapted to apply multi-phase AC or RF voltages or potentials to at least some of said electrodes and to switch the phase of the voltages or potentials applied to sequential electrodes along the device such that a pseudo-potential barrier moves along the device or to modulate the amplitude of the voltages or potentials in sequence along the device such that a pseudo-potential barrier moves along the device, wherein the potential barrier is configured to urge ions in a first direction through said separation device;

a second device arranged and adapted to provide a gas flow in a second direction which is substantially inclined or opposed to said first direction; and a controller arranged and adapted to control the first and second devices so that the potential barrier urges the ions against the gas flow such that the ions separate according to their mass to charge ratios.

The separation devices disclosed herein may have a number of general features.

For example, said plurality of electrodes may comprise ring electrodes, an ion tunnel or a plurality of electrodes each having an aperture through which ions are transmitted in use.

The plurality of electrodes may comprise axially segmented rod electrodes.

The plurality of electrodes may comprise a stack or array of planar, plate or mesh electrodes.

The separation device may comprise a third device for applying RF voltages to said plurality of electrodes so as to generate a radial pseudo-potential barrier which acts to confine ions radially within the separation device.

The first device may be arranged and adapted to apply said one or more transient DC voltages or potentials in said first direction wherein said first direction is either: (i) from an exit end of said separation device towards an entrance end of said separation device; or (ii) from an entrance end of said separation device towards an exit end of said separation device.

The second device may be arranged and adapted to cause said gas to flow in said second direction wherein said second direction is either: (i) from an exit end of said separation device towards an entrance end of said separation device; or (ii) from an entrance end of said separation device towards an exit end of said separation device.

The ions may be arranged to progressively exit from or elute from said separation device over a period of time either: (i) substantially in order of their ion mobility, collision cross section or differential ion mobility; (ii) substantially in reverse order of their ion mobility, collision cross section or differential ion mobility; (iii) substantially in order of their mass, mass to charge ratio or time of flight; or (ii) substantially in reverse order of their mass, mass to charge ratio or time of flight.

The present invention provides a mass spectrometer or ion mobility spectrometer comprising a separation device as described herein.

It is counter-intuitive that introducing a counterflow of gas with a separation device arranged to separate ions according to their mass to charge ratio should enhance the separation power of the separation device without substantially changing the mass to charge ratio correlation. It would be expected that a flow of gas opposed to the direction in which ions are urged by the travelling wave or one or more transient DC voltages or potentials would increase the number of ion-gas collisions per unit time (i.e. reduce the mean free path of the ions) and hence a proportion of the ions would reach terminal velocity and therefore separation would then revert to being with respect to ion mobility or collision cross section rather than correlated more strongly with mass to charge ratio. This hypothesis would be supported by the previous observation that the ion mobility separation power of a travelling wave device under the conditions of mobility separation may be improved by applying a counterflow of gas.

The fact that this does not occur can be explained by considering the velocity of the counterflow of gas required compared to the inherent thermal velocity of the target gas.

The mean free path of an ion in a buffer gas is inversely related to the relative velocity of the buffer gas and the ion. The velocity v(rms) of a gas molecule at room temperature (293K) is given by:

$$v(rms) = \sqrt{\frac{kT}{m}} \quad (1)$$

wherein k is Boltzmann's constant, m is mass and T is temperature in Kelvin.

For nitrogen the thermal velocity is ~680 m/s. Assuming a typical velocity of an ion in a travelling wave separation device to be 30 m/s then a counter gas flow of 30 m/s would completely stop this ion travelling along the device. This gas velocity is only 5% of the thermal velocity of the ions and hence has very little effect upon the mean free path.

In a mode of operation according to a preferred embodiment of the present invention the force due to the travelling wave or the application of the transient DC voltages or potentials to the electrodes is initially small compared to the force due to the gas flow and hence ions are trapped at the entrance of the ion mobility separator device. Ions can be prevented from being driven out of the ion mobility separator device by application of a DC or pseudo-potential barrier to either an entrance and/or exit electrode. In order to cause ions to elute from the device the travelling wave amplitude or the amplitude of the transient DC voltages or potentials applied to the electrodes may be increased and/or the velocity of the travelling wave or the rate at which the transient DC voltages or potentials are translated or applied along the length of the separation device may be decreased (increased) and/or the gas flow velocity may be decreased (increased).

It should be noted that according to a less preferred embodiment the gas may be arranged to flow from the entrance of the device to the exit of the device and the travelling wave or the transient DC voltages or potentials may be applied to the electrodes in a direction such that ions are urged by the travelling wave or applied transient DC voltages or potentials from the exit to the entrance of the device. According to this embodiment ions preferably elute from the exit of the device in reverse ion mobility order i.e. ions having a relatively low ion mobility elute before ions having a relatively high ion mobility.

According to the preferred embodiment the gas flow acts from the exit of the device to the entrance of the device and the travelling wave or transient DC voltage or potentials are preferably applied to electrodes from the entrance end of the device to the exit end of the device such that ions elute from the exit of the device in ion mobility order i.e. ions having a relatively high ion mobility elute before ions having a relatively low mobility.

According to a less preferred embodiment the direction of travel of the travelling wave or applied transient DC voltages or potentials applied to the electrodes and the gas flow direction may not be directly opposing i.e. may not be exactly 180° with respect to each other. Embodiments of the present invention are contemplated wherein there is simply a component of the force due to the gas flow which opposes the direction that ions are urged by the travelling wave or transient DC voltages or potentials.

According to embodiments of the present invention the angle θ between the direction of the flow of gas and the direction along which the travelling wave or the transient DC voltages or potentials are applied may be <10°, 10-20°, 20-30°, 30-40°, 40-50°, 50-60°, 60-70°, 70-80, 80-90°, 90-100°, 100-110, 110-120°, 120-130°, 130-140°, 140-150°, 150-160°, 160-170°, 170-180° or substantially 180°.

In this case the ions will disperse spatially and the device may be used as an ion mobility or mass to charge ratio filter.

From another aspect, the present invention provides a method of filtering ions comprising:

providing an ion filter comprising a plurality of electrodes;

applying one or more transient DC voltages or potentials to said electrodes so as to urge the ions in a first direction along the filter; and providing a flow of gas along the filter in a second direction so as to oppose the motion of the ions in the first direction;

wherein the first and second directions are angled with respect to each other at an angle other than being orthogonal such that ions having different physicochemical property values travel along different paths through the filter and such that only ions of a selected value or range of values of said physicochemical property exit the ion filter along a desired exit path.

The physicochemical property is preferably ion mobility or mass to charge ratio.

Preferably, only ions exiting the filter along said desired exit path are transmitted to a downstream ion analyser, ion detector or ion trap.

Preferably, the plurality of electrodes to which the one or more transient DC voltages or potentials is applied are parallel and aligned in a third direction, wherein the first and third directions are angled with respect to each other at an angle other than being orthogonal.

The method may comprise varying one or more or more operational parameters of the filter so as to select or vary the physicochemical property value(s) of the ions exiting the filter along the desired exit path, wherein the one or more operational parameters are: gas flow speed; gas flow direction; transient DC voltage or potential speed along the filter; transient DC voltage or potential amplitude; and transient DC voltage or potential direction of travel.

The force for driving ions in the first direction may be provided by a multiphase AC or RF voltage being applied to the electrodes, rather than one or more transient DC voltages or potentials.

Accordingly, from another aspect the present invention provides a method of filtering ions comprising:

providing an ion filter comprising a plurality of electrodes;

applying multi-phase AC or RF voltages or potentials to at least some of said electrodes, switching the phase of the voltages or potentials applied to sequential electrodes along the filter such that a pseudo-potential barrier moves along the filter or modulating the amplitude of the voltages or potentials in sequence along the filter such that a pseudo-potential barrier moves along the filter, wherein the potential barrier urges the ions in a first direction along the filter; and providing a flow of gas along the filter in a second direction so as to oppose the motion of the ions in the first direction;

wherein the first and second directions are angled with respect to each other at an angle other than being orthogonal such that ions having different physicochemical property values travel along different paths through the filter and such that only ions of a selected value or range of values of said physicochemical property exit the ion filter along a desired exit path.

The physicochemical property may be ion mobility or mass to charge ratio.

Preferably, only ions exiting the filter along said desired exit path are transmitted to a downstream ion analyser, ion detector or ion trap.

Preferably, the plurality of electrodes to which the AC or RF voltages or potentials are applied are parallel and aligned in a third direction, wherein the first and third directions are angled with respect to each other at an angle other than being orthogonal.

The method preferably comprises varying one or more or more operational parameters of the filter so as to select or vary the physicochemical property value(s) of the ions exiting the filter along the desired exit path, wherein the one or more operational parameters are: gas flow speed; gas flow direction; potential barrier speed; potential barrier amplitude; and potential barrier direction of travel.

The present invention also provides a method of mass spectrometry or ion mobility spectrometry comprising a method of filtering ions as described herein.

The present invention also provides an ion filter comprising:

a plurality of electrodes;

a first device arranged and adapted to apply one or more transient DC voltages or potentials to said electrodes so as to urge the ions in a first direction along the filter;

a second device arranged and adapted to provide a gas flow along the filter in a second direction so as to oppose the motion of the ions in the first direction, wherein the first and second directions are angled with respect to each other at an angle other than being orthogonal; and a controller arranged and adapted to control the first and second devices so that the one or more transient DC voltages or potentials urge the ions against the gas flow such that ions having different physicochemical property values travel along different paths through the filter and such that only ions of a selected value or range of values of said physicochemical property exit the ion filter along a desired exit path.

The present invention also provides an ion filter comprising:
a plurality of electrodes;
a first device arranged and adapted to apply multi-phase AC or RF voltages or potentials to said electrodes, to switch the phase of the voltages or potentials applied to sequential electrodes along the filter such that a pseudo-potential barrier moves along the filter or modulating the amplitude of the voltages or potentials in sequence along the filter such that a potential barrier moves along the filter, wherein the potential barrier urges the ions in a first direction along the filter;
a second device arranged and adapted to provide a gas flow along the filter in a second direction so as to oppose the motion of the ions in the first direction, wherein the first and second directions are angled with respect to each other at an angle other than being orthogonal; and
a controller arranged and adapted to control the first and second devices so that the potential barrier urges the ions against the gas flow such that ions having different physicochemical property values travel along different paths through the filter and such that only ions of a selected value or range of values of said physicochemical property exit the ion filter along a desired exit path.

The present invention provides a mass spectrometer or ion mobility spectrometer comprising an ion filter as described herein.

According to a preferred embodiment the force provided by the travelling wave or by the application of the transient DC voltages or potentials to the electrodes and the force due to the moving gas may be arranged to balance each other out such that at least some ions are substantially retained within the ion guide for a period of time and may be caused to elute from the ion guide by adjusting at least one of the parameters of the travelling wave or transient DC voltages or potentials applied to the electrodes and/or one or more parameters of the gas flow.

According to an embodiment the mass spectrometer may further comprise:
(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; and (xxvi) a Solvent Assisted Inlet Ionisation ("SAII") ion source; and/or
(b) one or more continuous or pulsed ion sources; and/or
(c) one or more ion guides; and/or
(d) one or more ion mobility separation devices and/or one or more Field Asymmetric Ion Mobility Spectrometer devices; and/or
(e) one or more ion traps or one or more ion trapping regions; and/or
(f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or
(g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or
(h) one or more energy analyzers or electrostatic energy analyzers; and/or
(i) one or more ion detectors; and/or
(j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or
(k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer further comprises a device arranged and adapted to supply an AC or RF voltage to the electrodes. The AC or RF voltage preferably has an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage preferably has a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The mass spectrometer may also comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

BRIEF DESCRIPTION OF THE DRAWINGS

Various embodiments of the present invention together with other arrangements given for illustrative purposes only will now be described, by way of example only, and with reference to the accompanying drawings in which:

FIG. 11 shows another embodiment of the present invention similar to the embodiment shown in FIG. 1 except that the gas flow is in a direction from the entrance to the exit of the ion mobility separator and the travelling wave or transient DC voltages or potentials are applied in a direction from the exit to the entrance of the ion mobility separator.

DETAILED DESCRIPTION OF PREFERRED EMBODIMENT

A preferred embodiment of the present invention will now be described with reference to FIG. 1A.

Figure 1A:
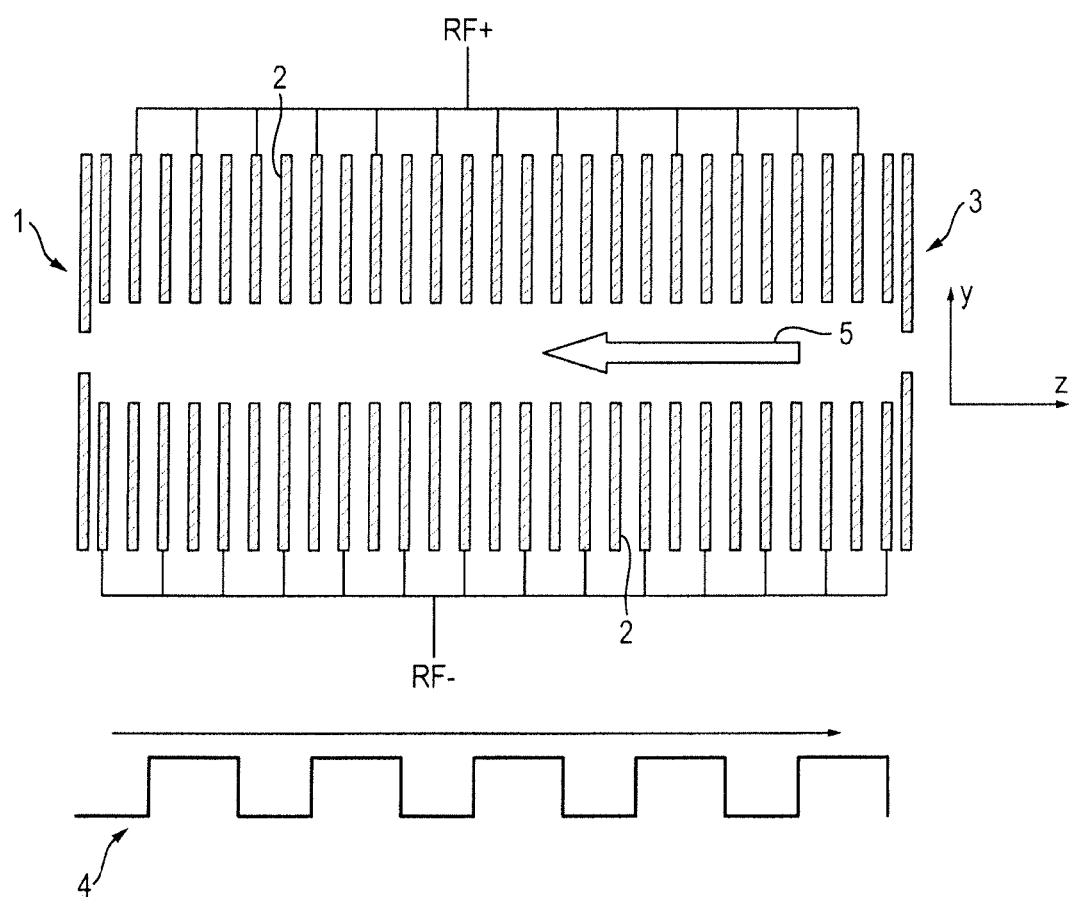
FIG. 1A shows an ion mobility separator according to a preferred embodiment wherein ions are urged from the entrance to the exit of the ion mobility separator by applying a plurality of transient DC voltages or potentials to the electrodes forming the ion mobility separator and wherein an opposed or counterflow of gas is also applied so that the gas forces ions back towards the entrance and FIG. 1B shows an individual ring electrode of the preferred device.

FIG. 1A shows a preferred embodiment of the invention wherein an ion mobility separator or other separation device is provided comprising an RF confined ring stack arrangement. The RF ring stack preferably comprises an entrance electrode 1, a series of intermediate ring electrodes 2 and an exit electrode 3. Opposite phases of an AC potential oscillating at RF frequency are preferably applied to alternate ring electrodes 2 in order to produce a radial RF confining force or pseudo-potential. The ring stack preferably comprises a plurality of electrodes each having an aperture through which ions are transmitted in use. Alternative embodiments are also contemplated wherein the ion mobility separator or other separation device comprises a segmented multipole rod set or a plurality of planar electrodes arranged generally in a plane parallel to the plane in which ions travel through the device.

Figure 1B:
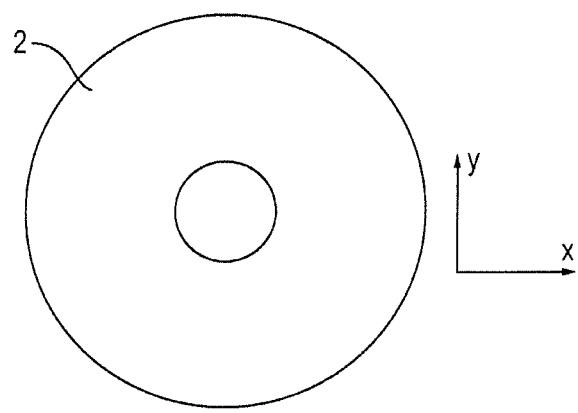

FIG. 1A shows the preferred device in the y,z dimension and FIG. 1B shows an individual ring electrode 2 in the x,y dimension.

In operation ions are preferably urged from the entrance end 1 to the exit end 3 of the device by applying a travelling DC wave or a plurality of transient DC voltages or potentials 4 to the ring electrodes 2 forming the ion mobility separator or other separation device. A counterflow of gas 5 is preferably provided in the opposite direction to the direction of travel of the travelling DC wave or the direction in which the plurality of transient DC voltages or potentials 4 progress along the length of the ion mobility separator or other separation device. As will be understood, although the separation device is preferably operated in a mode of operation wherein ions are separated temporally according to their ion mobility or collision cross section an advantageous aspect of the present invention is that the separation device may also be easily operated in a mode of operation wherein ions are separated temporally according to their mass or mass to charge ratio. A particularly preferred aspect of the present invention is that the separation device may be readily switched between a first mode wherein ions are temporally separated according to their ion mobility or collision cross section and a second mode wherein ions are temporally separated according to their mass or mass to charge ratio.

A SIMION 8® model of a travelling wave ion mobility device comprising a plurality of ring electrodes was constructed in order to model the behaviour of the preferred device. The inside diameter of the ring electrodes was modelled as being 5 mm. The ring plates or electrodes were modelled as being 0.5 mm thick and arranged with a 1 mm inter plate spacing. The ring electrodes were modelled as being supplied with an AC potential oscillating at 2.7 MHz with an amplitude of 250 V peak to peak. Opposite phases of RF were modelled as being applied to adjacent plates or electrodes.

Transient DC voltages or potentials were modelled as being applied to two pairs of plate electrodes in a six plate pair repeat pattern. For each set of six plate pairs at a given time the same plate pair in a sequence of 67 pairs was applied with the transient DC voltage or potential. A DC travelling wave was set up by applying a transient DC voltage or potential to each plate pair in turn. Therefore, in one time step the potential increments by one plate pair i.e. 3 mm.

The velocity of the DC travelling wave can be controlled by changing the time between switching the DC voltage or potential between each plate pair. For example, switching the DC voltage or potential between adjacent plate pairs in the sequence every 10 µs will result in a travelling wave velocity of 300 m/s.

The trajectory of ensembles of singly and doubly charged ions with a range of mass to charge ratios and collision cross sections were modelled starting at the entrance end of the ion guide. The exit time of ions exiting from the ion guide was recorded. The total length along which ions were modelled as travelling was 185 mm. The mean drift times and the standard deviation of the mean drift times were recorded.

The collision cross-section CCS of the ions was estimated as follows:

$$CCS = \pi^* \left[ \frac{D_{ion}}{2} + \frac{D_{gas}}{2} \right]^2 \quad (2)$$

wherein $D_{ion}$ is the hard sphere diameter of the ions and was estimated from:

$$D_{ion} = 1.436^* \sqrt[3]{M_{ion}} \quad (3)$$

wherein $M_{ion}$ is the mass of the ion and wherein:

$$D_{gas} = 1.436^* \sqrt[3]{M_{gas}} \quad (4)$$

wherein $M_{gas}$ is the mass of the IMS buffer gas.

In all cases helium was modelled as being the buffer gas.

To emulate the motion of the ions in a gas filled device a hard sphere collision gas model was used.

A list of the masses and cross sections used for each ensemble of ions is detailed below in Tables 1 and 2. Table 1 details the mass and collision cross section of singly charged ions which were modelled and Table 2 details the mass and collision cross section of doubly charged ions which were modelled.

In addition, the trajectories of a third set of singly charged ions having different collision cross sections were also examined. These ensembles of ions differed from those in Table 1 in that they were twice the mass and their collision cross section values were scaled by a factor of 0.75. A list of the masses and cross sections of the third set of ions is shown in Table 3 below.

To compare the data sets calculated under different conditions two figures of merit were used.

Firstly, a measure of the average separation RMob between ions having the same mass to charge ratio but different collision cross sections ("CCS") may be used wherein:

$$RMob = \sum_n \frac{\sqrt{[DTx(n) - DTy(n)]^2}}{2.35 * 0.5(SDx(n) + SDy(n))} * \frac{1}{n} \quad (5)$$

wherein DTx and DTy are pairs of calculated drift time values for ions having the same mass to charge ratio in Tables 1 and 2 or in Tables 1 and 3.

A higher value of RMob indicates separation with stronger ion mobility dependence.

The second figure of merit is a measure of the average separation RMass between drift times calculated for consecutive mass to charge ratio values in Table 1 for singly charged ions:

$$RMass = \sum_{n=0}^{n-1} \frac{[DTz(n+1) - DTz(n)]}{2.35 * 0.5(SDx(n) + SDy(n))} * \frac{1}{n} \quad (6)$$

wherein DTz is the drift time calculated for the collision cross section and mass to charge ratio values given in Table 1.

RMass is a measure of the mass to charge ratio separating power. A higher value of RMass indicates a higher mass separating power.

The relative changes in these two figures of merit gives an indication of the extent to which ions are separated due to differences in their ion mobility or due to differences in their mass to charge ratio.

TABLE 1

| Mass | CCS ($A^2$) | Charge state |
|---|---|---|
| 100.0 | 62.83969 | 1+ |
| 290.0 | 109.0725 | 1+ |
| 480.0 | 143.6271 | 1+ |
| 670.0 | 173.0813 | 1+ |
| 860.0 | 199.442 | 1+ |
| 1050.0 | 223.6533 | 1+ |
| 1240.0 | 246.2517 | 1+ |
| 1430.0 | 267.5781 | 1+ |
| 1620.0 | 287.8655 | 1+ |
| 1810.0 | 307.2821 | 1+ |
| 2000.0 | 325.9539 | 1+ |

TABLE 2

| Mass | CCS ($A^2$) | Charge state |
|---|---|---|
| 200 | 89.53889 | 2+ |
| 580 | 159.5992 | 2+ |
| 960 | 212.4126 | 2+ |
| 1340 | 257.618 | 2+ |
| 1720 | 298.1845 | 2+ |
| 2100 | 335.5159 | 2+ |
| 2480 | 370.4129 | 2+ |
| 2860 | 403.386 | 2+ |
| 3240 | 434.7848 | 2+ |
| 3620 | 464.8619 | 2+ |
| 4000 | 493.8072 | 2+ |

TABLE 3

| Mass | CCS ($A^2$) | Charge state |
|---|---|---|
| 200 | 47.12977 | 1+ |
| 580 | 81.80441 | 1+ |
| 960 | 107.7203 | 1+ |
| 1340 | 129.811 | 1+ |
| 1720 | 149.5815 | 1+ |
| 2100 | 167.74 | 1+ |
| 2480 | 184.6888 | 1+ |
| 2860 | 200.6836 | 1+ |
| 3240 | 215.8991 | 1+ |
| 3620 | 230.4615 | 1+ |
| 4000 | 244.4654 | 1+ |

Figure 2:
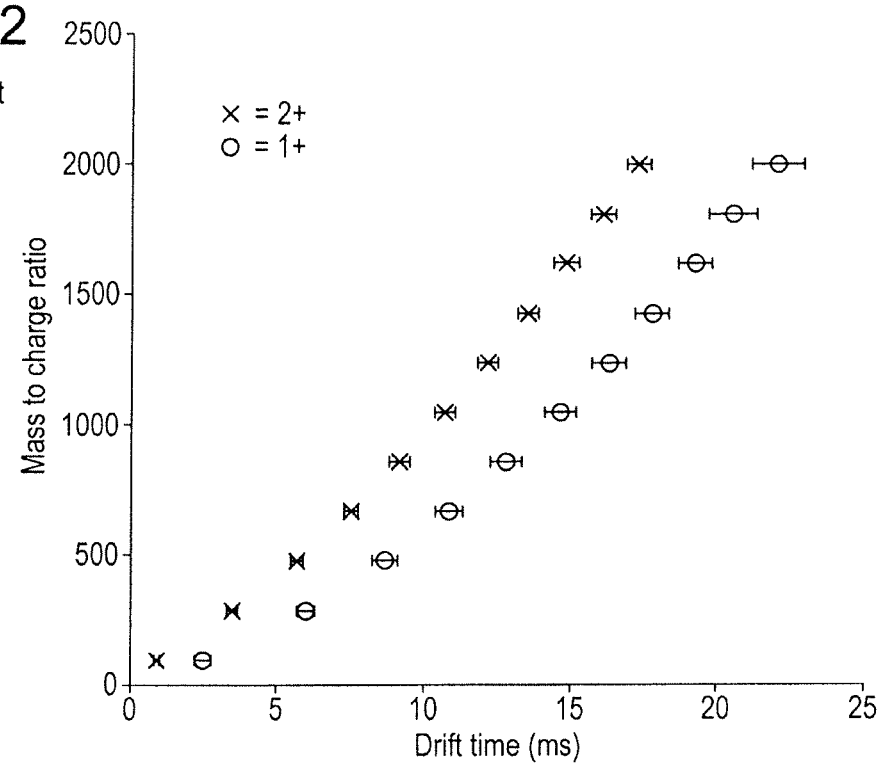
FIG. 2 shows a plot of mass to charge ratio versus drift time for ions which were modelled using a conventional travelling wave ion mobility separator operating under conventional ion mobility conditions without a counterflow of gas and with a travelling wave velocity of 300 m/s.

FIG. 2 shows a plot of mass to charge ratio versus drift time for the ions detailed above using standard travelling wave ion mobility conditions. The error bars are the standard deviation of drift times for each ensemble of ions and give an indication of the separating power of the preferred device at FWHM definition.

The data shown in FIG. 2 was obtained when the gas was static and at a pressure of 1 Torr of helium. The travelling wave speed was modelled as being 300 m/s and the amplitude of the transient DC voltage was ramped from 2 V at a rate of 0.2 V/ms.

The two trend lines illustrate the separation of doubly and singly charged ions at the same mass to charge ratio value due to the differences in their ion mobility. For this data RMob was determined to be 3.8 and RMass was determined to be 1.9.

This reflects the relatively large difference in ion mobility between ions of the same mass to charge ratio and different charge state compared with the smaller difference in mobility between consecutive singly charged ions in Table 1.

Figure 3:
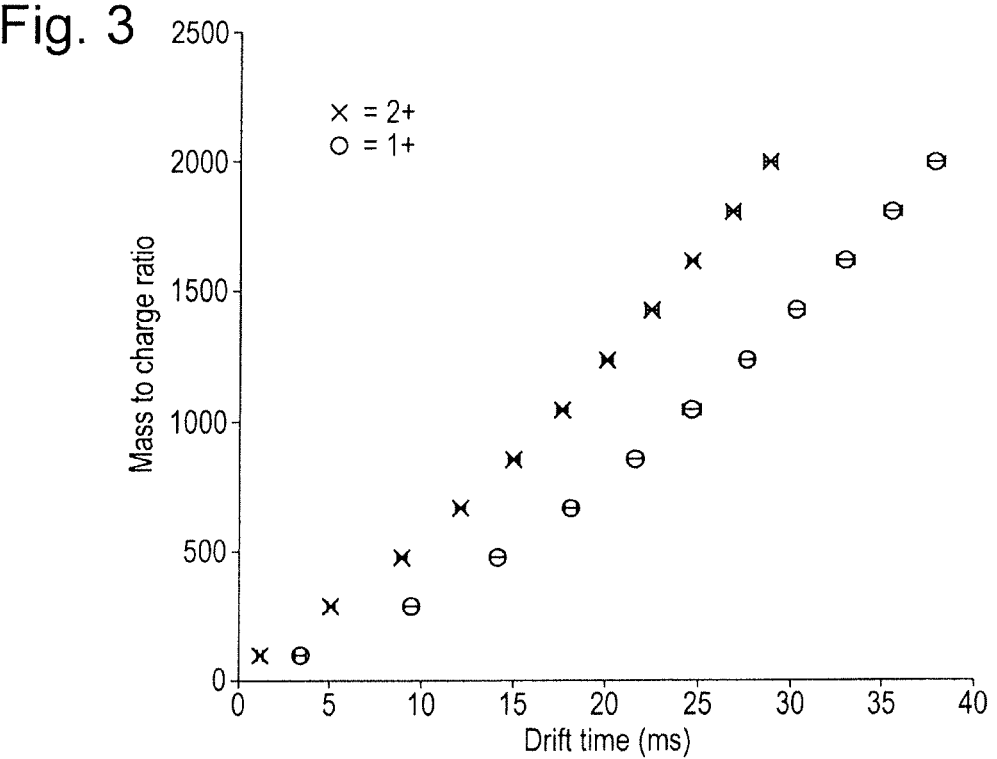
FIG. 3 shows a plot of mass to charge ratio versus drift time for the same ions as were modelled in FIG. 2 but in accordance with a preferred embodiment of the present invention wherein a counterflow of gas was utilised and with a travelling wave velocity of 300 m/s.

FIG. 3 shows a plot of mass to charge ratio versus drift time for the ions which were modelled in FIG. 2 under the same pressure of 1 Torr helium but in accordance with a preferred embodiment of the present invention wherein a gas was modelled as flowing at a velocity of 20 m/s in a direction opposing the motion of the ions. The gas was modelled as being at a pressure of 1 Torr of helium. The travelling wave speed was modelled as being 300 m/s and the amplitude of the transient DC voltage was ramped from 2 V at a rate of 0.2 V/ms. For this data RMob was determined to be 8.1 and RMass was determined to be 3.8.

It is clear from the different drift time scales shown in FIGS. 2 and 3 that both the separation between ions of the same mass to charge ratio and different charge states and between ions of the same charge state and different masses have increased by substantially the same proportion (2x) due to the application of the low velocity counterflow of gas. This indicates that the preferred device benefits from an increased ion mobility resolution performance. The overall drift time (DT) increased from 22 ms to 37 ms.

Figure 4:
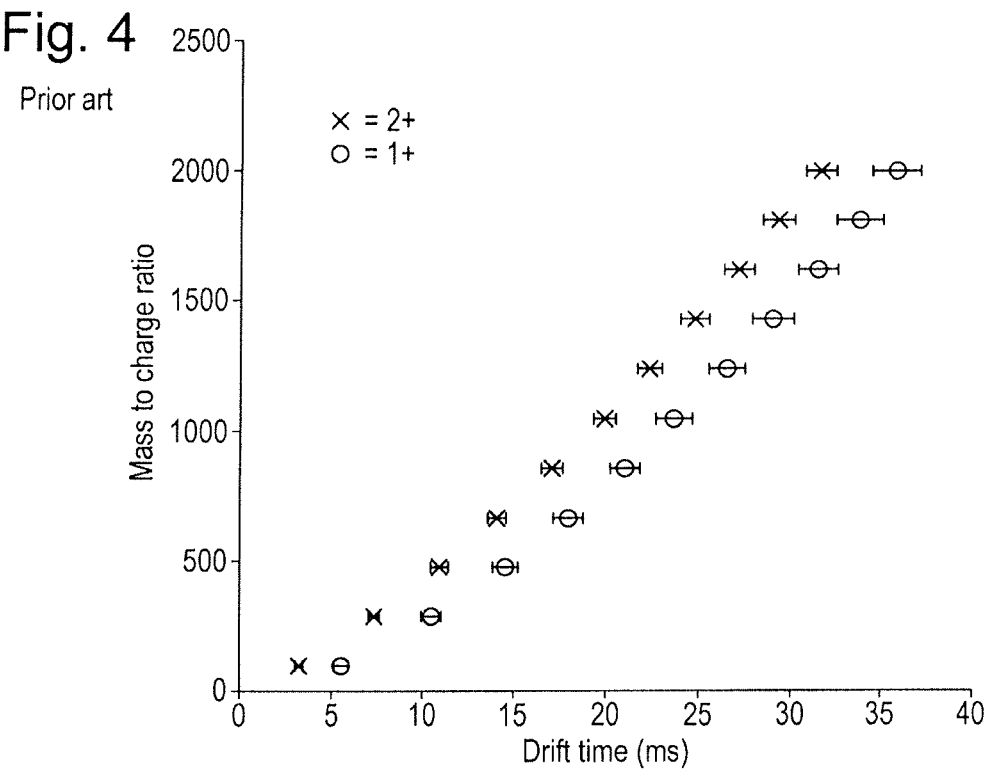
FIG. 4 shows a plot of mass to charge ratio versus drift time for the ions which were modelled in FIG. 2 under the same pressure of 1 Torr helium without a counterflow of gas and with a travelling wave velocity of 600 m/s.

FIG. 4 shows a plot of mass to charge ratio versus drift time for the ions modelled in FIG. 2 under the same pressure of 1 torr helium. In this case the gas was static and at a pressure of 1 Torr of helium. The travelling wave speed was modelled as being increased to 600 m/s and the amplitude of the transient DC voltage was ramped from 2 V at a rate of 0.2 V/ms. For this data RMob was determined to be 2.4 and RMass was determined to be 1.7.

The maximum drift time is similar to that shown in FIG. 3 for a 20 m/s counterflow of gas. However, compared to FIG. 2 the separation between the different charge states has reduced indicating lower mobility separation. By contrast, the separation between different masses of the same charge state has reduced by a smaller proportion. This demonstrates that applying a counterflow of gas does not have the same effect as increasing the travelling wave velocity even though both methods result in a similar increase in the drift time.

Figure 5:
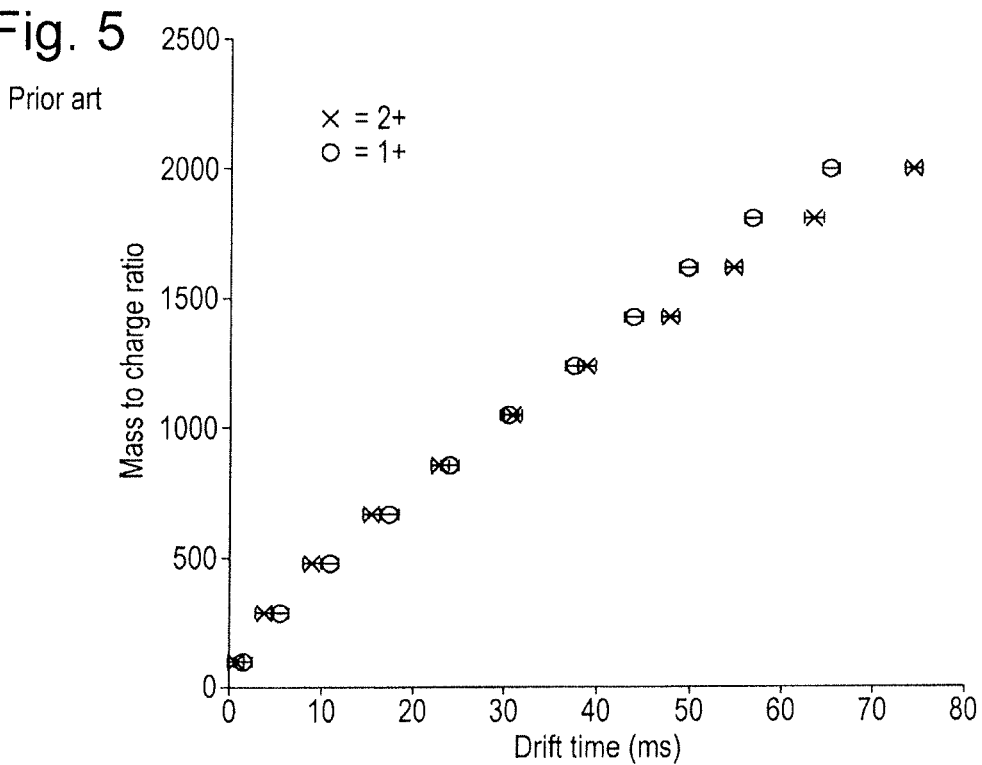
FIG. 5 shows a plot of mass to charge ratio versus drift time for the ions which were modelled in FIG. 2 under the same pressure of 1 Torr helium without a counterflow of gas but wherein the travelling wave velocity was increased to 1500 m/s.

FIG. 5 shows a plot of mass to charge ratio versus drift time for the ions modelled above in relation to FIG. 2 under the same pressure of 1 Torr helium. In this case the gas was again static and at a pressure of 1 Torr of helium. The travelling wave speed was further increased to 1500 m/s and the amplitude of the transient DC voltage was ramped from 8 V at a rate of 0.2 V/ms. For this data RMob was determined to be 1.3 and RMass was determined to be 2.3.

When a faster travelling wave was applied the drift time increased to a maximum of 80 ms. It is also clear that the two trend lines corresponding to singly and doubly charged ions have reduced in separation. This is reflected by the low value of RMob. However, the separation between singly charged ions of different mass to charge ratio has increased as indicated by a RMass value of 2.3 compared with a RMass value of 1.9 for the arrangement shown in FIG. 2. This indicates that separation is no longer dominated by the mobility of the ions and is now substantially related to the mass to charge ratio of the ions.

To confirm that at higher travelling wave speeds separation is dominated by mass to charge ratio rather than ion mobility, ions of the same mass to charge ratio but with different cross sections were examined.

Figure 6:
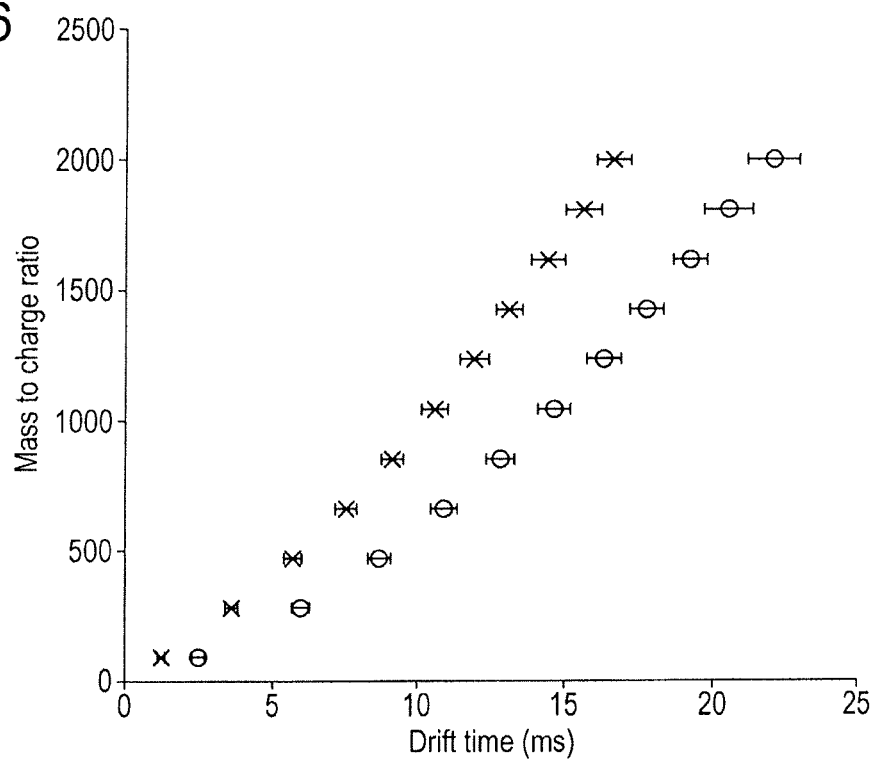
FIG. 6 shows a plot of mass to charge ratio versus drift time for the ions detailed in Tables 1 and 3 below with a static gas and a travelling wave velocity of 300 m/s.

FIG. 6 shows a plot of mass to charge ratio versus drift time for the ions listed in Tables 1 and 3. In this case the gas was static and at a pressure of 1 Torr of helium. The travelling wave speed was 300 m/s and the amplitude of the transient DC voltage was ramped from 2 V at a rate of 0.2 V/ms. For this data RMob was determined to be 3.4 and RMass was determined to be 1.9.

This is very similar to the data in FIG. 2. However, the ions are now all singly charged ions with the same mass to charge ratio value and differ only in collision cross section ("CCS").

Figure 7:
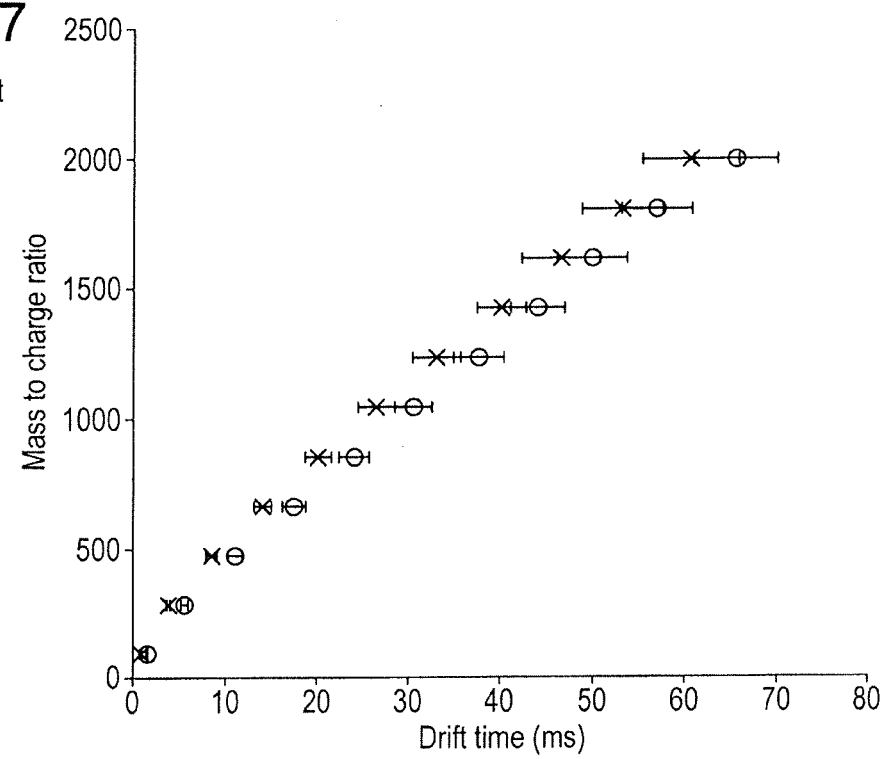
FIG. 7 shows a plot of mass to charge ratio versus drift time for the ions shown in FIG. 6 again with a static gas but wherein the travelling wave velocity was increased to 1500 m/s.

FIG. 7 shows a plot of mass to charge ratio versus drift time for the ions modelled in FIG. 6. In this case the gas was static and at a pressure of 1 Torr of helium. The travelling wave speed was increased to 1500 m/s and the amplitude of the transient DC voltage was ramped from 8 V at a rate of 0.2 V/ms. For this data RMob was determined to be 1.3 and RMass was determined to be 2.3.

This is very similar to the data shown in FIG. 5 confirming that separation is dominated by mass to charge ratio and not ion mobility or collision cross section ("CCS") at this higher wave velocity.

Figure 8:
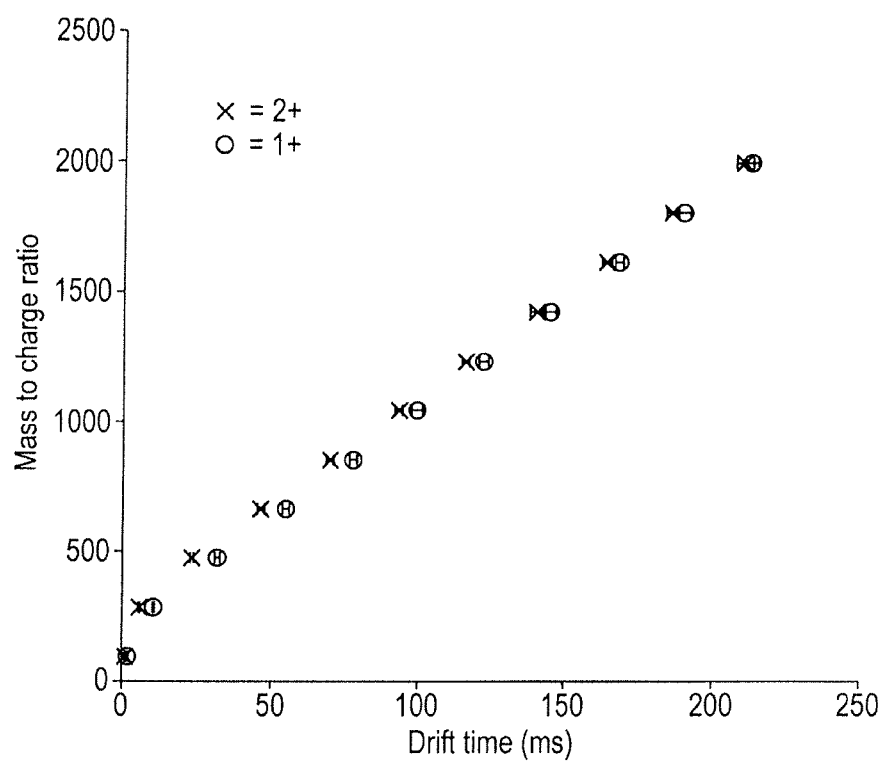
FIG. 8 shows a plot of mass to charge ratio versus drift time for the ions shown in FIG. 5 but with a counterflow of gas and wherein the travelling wave velocity was 1500 m/s.

FIG. 8 shows a plot of mass to charge ratio versus drift time for the ions modelled in FIG. 5. In this case the gas was flowing at a velocity of 20 m/s in a direction opposing the motion of the ions and at a pressure of 1 Torr of helium. The travelling wave speed was 1500 m/s and the amplitude of the transient DC voltage was ramped from 8V at a rate of 0.2 V/ms. For this data RMob was determined to be 2.4 and RMass was determined to be 6.6.

It is clear from the increase in RMass that the mass to charge ratio separation power of this device has been increased by a factor of nearly 3 times compared to the arrangement described above with reference to FIG. 5 due to the application a counterflow of gas while the separation attributed to ion mobility has increased only by a factor of x 1.04. The maximum drift time has also increased by a factor of x3.

This demonstrates that applying a counterflow of gas to a travelling wave ion separation device operated in a mass or mass to charge ratio separation mode with a fast travelling wave velocity advantageously increases the mass or mass to charge ratio separating power of the device.

Figure 9A:
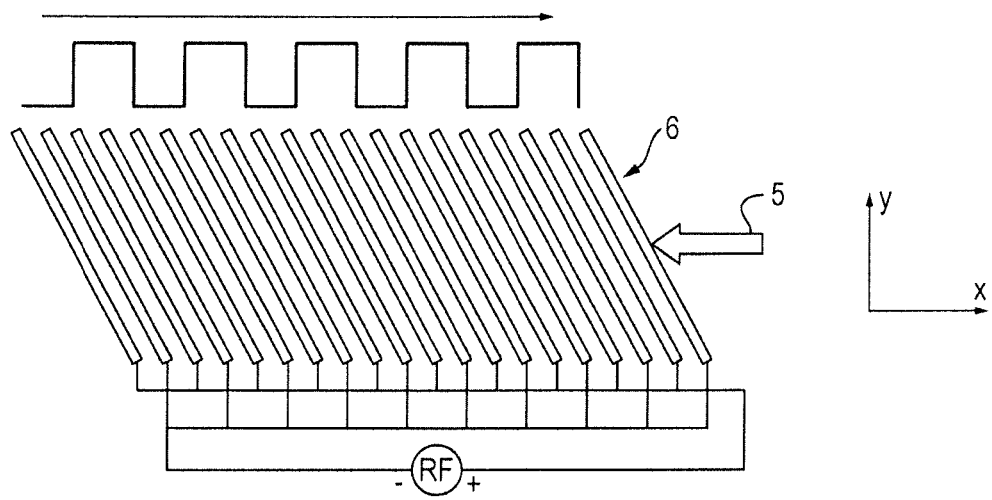
FIG. 9A shows an ion separation device according to an alternative embodiment of the present invention in the (y,z) plane wherein a counterflow of gas was provided but wherein the flow of gas was arranged in a direction which was not completely opposed to the direction along which the ions are urged by the travelling wave.
Figure 9B:
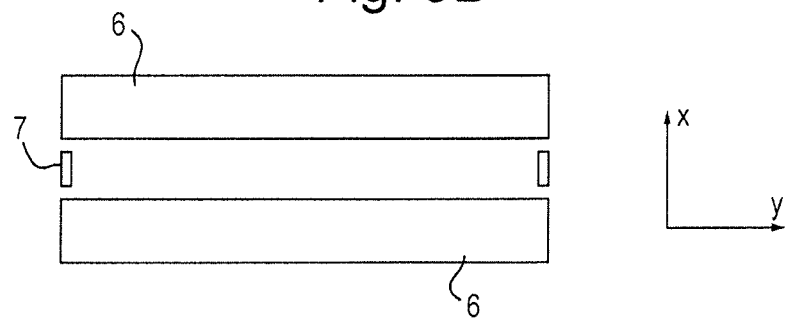
FIG. 9B shows the device in the (x,y) plane
Figure 9C:
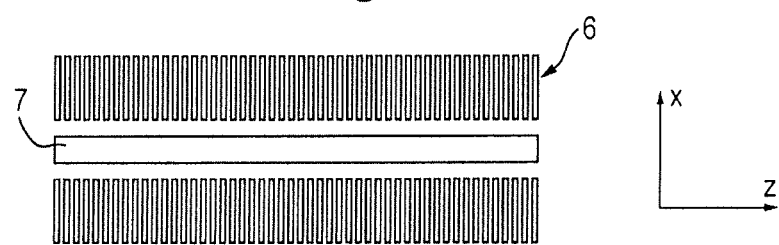
FIG. 9C shows the device in the (x,z) plane.

FIGS. 9A-9C illustrate a further embodiment of the present invention wherein the counterflow of gas may not be completely opposed to the direction in which the ions are urged by the travelling wave.

FIG. 9A shows the device in the (y,z) plane. The device is constructed from two planar arrays of plate like electrodes 6 which are preferably inclined or at an angle with respect to the direction of the gas flow 5. Ions are preferably confined in the y direction by applying alternating phases of a RF frequency AC potential to the plate electrodes. This forms a pseudo-potential confining force in the y direction. Ions may be confined in the x direction, if required, by electrodes running down the z length of the device in the z direction to which a DC confining potential is applied. FIG. 9B shows the device in the (x,y) direction and shows planar electrodes 6 and DC electrodes 7. FIG. 9C shows the device in the (x,z) plane. In operation a DC travelling wave is preferably applied to the planar electrodes 6.

Figure 10A:
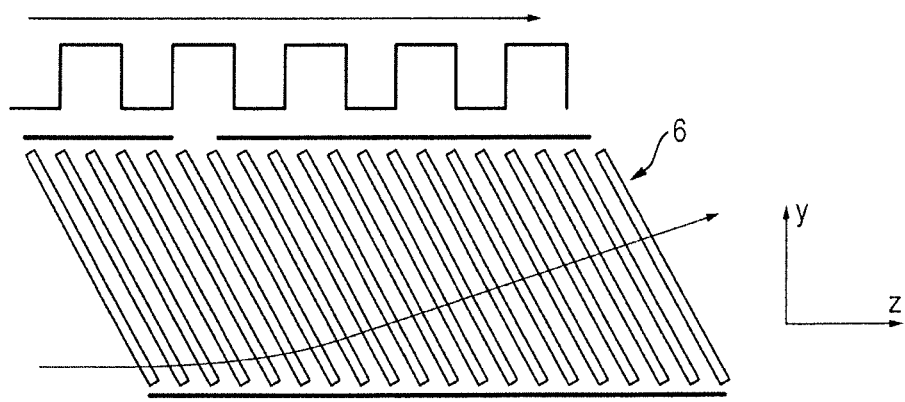
FIG. 10A shows the same device in the (y,z) plane indicating the path which ions take through the device in the absence of a counterflow of gas

FIG. 10A shows the same device in the (y,z) plane and indicates the path which ions preferably take through the device in the absence of a counterflow of gas. Ions may be introduced continuously or as a pulse. All ions preferably follow the same path. If ions are introduced as a packet or pulse then the ions will preferably separate according to ion mobility or mass to charge ratio depending on the velocity of the travelling wave and will exit the device as shown or will impinge on one of the electrodes.

Figure 10B:
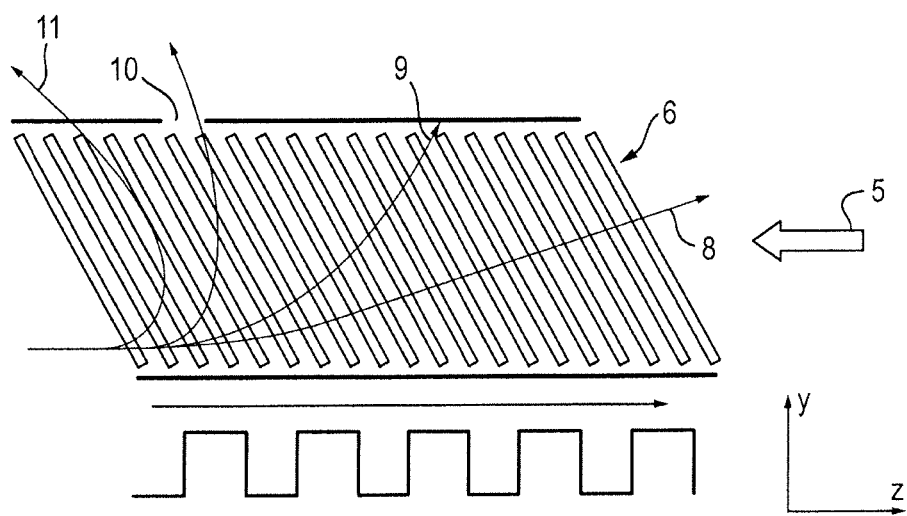
FIG. 10B shows the device in the (y,z) plane indicating the path which ions take through the device in the presence of a counterflow of gas.

FIG. 10B shows the path of ions in the presence of a counterflow of gas 5. Ions having a specific ion mobility or mass to charge ratio may be arranged to exit the device at an exit orifice 10 and impinge upon an ion detector or be onwardly transmitted to another device. Ions of lower mobility or higher mass to charge ratio value 11 will not travel as far through the device. These ions may be arranged to be discarded. Ions of higher mobility or lower mass to charge ratio 8,9 preferably travel further though the device and may also be discarded.

The device as described above may be configured to provide high resolution ion mobility filtering or mass to charge ratio filtering depending of the velocity of the travelling wave as described. The device may be used with introduction of either a pulsed or continuous beam of ions.

By varying the amplitude or speed of the travelling wave or the velocity of the gas flow ions of differing properties may be arranged to exit the device.

FIG. 11 shows another embodiment of the device. This embodiment is identical to that shown in FIG. 1 except in this case the gas flow 5 is in a direction from the entrance 1 to the exit of the device 3. A travelling wave voltage is preferably applied to the electrodes which preferably acts to oppose the gas flow 4 urging ions from the exit 3 to the entrance of the device 1. In operation the amplitude and velocity of the travelling wave is such that ions of interest cannot be overtaken by the travelling wave and are hence driven towards the entrance of the device. Ions are effectively trapped with substantially no separation near to the entrance of the device by a combination of gas flow and opposing travelling wave. Ions are preferably arranged to travel from this trapping region to the exit of the device by increasing the velocity of the travelling wave or the rate at which transient DC voltages or potentials are applied to the electrodes such that ions of low mobility start to be overtaken by the travelling wave or transient DC voltages or potentials. By scanning or stepping the velocity of the travelling wave or transient DC voltages or potentials from low velocity to high velocity ions will preferably exit the device in ascending order of ion mobility or collision cross section. Full high resolution ion mobility separation spectra may be produced. Less preferably the amplitude of the travelling wave or transient DC voltages or potentials may be reduced to allow ions to exit the device or a combination of amplitude and velocity may be used.

With a continuously introduced ion beam this approach may be used to provide a high mobility cut off mode of operation.

This embodiment can be realised in the intermediate pressure transfer region between an atmospheric ion source and a downstream analytical device or mass spectrometer. In this region the direction of gas flow is from high pressure at the ion source or ion entrance to low pressure at the exit of the device. Ions may be trapped using a travelling wave or transient DC voltages or potentials and sequentially scanned out in order of their ion mobility in this region of the mass spectrometer.

It may be advantageous in some cases to operate the device in an intermediate separation mode where separation comprises a component of ion mobility and also a component of mass to charge ratio rather than in a situation where separation is predominantly related to ion mobility, collision cross section or predominantly related to mass to charge ratio.

The device can be stepped discreetly or ramped continuously between mass to charge ratio and ion mobility separation depending on the desired mode of operation.

Although the present invention has been described with reference to preferred embodiments, it will be understood by those skilled in the art that various changes in form and detail may be made without departing from the scope of the invention as set forth in the accompanying claims.

The invention claimed is:

1. A method of separating ions, comprising:
providing a separation device comprising a plurality of electrodes;
either (i) applying one or more transient DC voltages or potentials to at least some of said electrodes in order to urge ions in a first direction through said separation device; or (ii) applying multi-phase AC or RF voltages or potentials to at least some of said electrodes, switching the phase of the voltages or potentials applied to sequential electrodes along the device such that a pseudo-potential barrier moves along the device or modulating the amplitude of the voltages or potentials in sequence along the device such that a pseudo-potential barrier moves along the device, wherein the potential barrier urges ions in a first direction through said separation device; and
providing a gas flow in a second direction which is substantially inclined or opposed to said first direction.

2. The method of claim 1, wherein the method is a method of separating ions according to mass to charge ratio.

3. The method of claim 1, further comprising either:
(i) performing a first mode of operation in which said one or more transient DC voltages are swept, translated or sequentially applied along at least a portion of the axial length of said separation device with a first velocity so as to cause ions to be separated according to their ion mobilities; and performing a second mode of operation in which said one or more transient DC voltages are swept, translated or sequentially applied along at least a portion of the axial length of said separation device with a second velocity that is higher than said first velocity so as to cause ions to be separated according to their mass to charge ratios; wherein said gas flow is provided during said first and second modes; or
(ii) performing a first mode of operation in which said one or more AC or RF voltages or potentials are applied along at least a portion of the axial length of said separation device so that said potential barrier moves along the device at a first velocity so as to cause ions to be separated according to their ion mobilities; and performing a second mode of operation in which said one or more AC or RF voltages or potentials are applied along at least a portion of the axial length of said separation device so that said potential barrier moves along the device at a second velocity that is higher than said first velocity so as to cause ions to be separated according to their mass to charge ratios;
wherein said gas flow is provided during said first and second modes.

4. The method of claim 3, wherein said second mode causes ions to exit the separation device in order of increasing or decreasing mass to charge ratio; wherein the second mode further comprises: transmitting the ions, whilst separated, from the separation device to a downstream ion analyser; and varying the operation of the ion analyser as a function of time, based on and in synchronism with the mass to charge ratios of the ions exiting the separation device and being received at the ion analyser.

5. The method of claim 4, wherein the ion analyser comprises an ion filter that only transmits ions having a certain value or range of values of a physicochemical property at any given time during, and wherein the value or range of values transmitted by the ion filter is varied with time in said second mode based on and in synchronism with the mass to charge ratios of the ions exiting the separation device and being received at the ion analyser.

6. The method of claim 4, wherein the ion analyser is a discontinuous ion analyser that receives ions from the separation device and repeatedly pulses ions into an analysis region; and wherein the duration of time between the pulses is varied as a function of time, based on and in synchronism with the mass to charge ratios of the ions exiting the separation device and being received at the ion analyser; or wherein the duration of time between any given ion exiting the separation device and being pulsed into the analysis region is varied as a function of time, based on and in synchronism with the mass to charge ratios of the ions exiting the separation device and being received at the ion analyser.

7. The method of claim 6, wherein the ion analyser is a Time of Flight mass analyser and the analysis region is a Time of Flight region.

8. The method of claim 3, wherein said first mode causes ions to exit the separation device in order of increasing or decreasing ion mobility; wherein the first mode further comprises: transmitting the ions, whilst separated, from the separation device to a downstream ion analyser; and varying the operation of the ion analyser as a function of time, based on and in synchronism with the ion mobilities of the ions exiting the separation device and being received at the ion analyser.

9. The method of claim 8, wherein in the first mode the ion analyser comprises an ion filter that only transmits ions having a certain value or range of values of a physicochemical property at any given time, and wherein the value or range of values transmitted by the ion filter is varied with time in said first mode based on and in synchronism with the ion mobilities of the ions exiting the separation device and being received at the ion analyser.

10. The method of claim 3, wherein ions having the same mass to charge ratio but differing ion mobilities are separated in the first mode; and/or ions having the same ion mobility but differing mass to charge ratios are separated in the second mode.

11. The method of claim 3, wherein in the first mode the one or more DC voltage or potential barriers and counter gas flow cause the ions to reach their terminal velocities; and in second mode the one or more DC voltage or potential barriers and counter gas flow do not cause the ions to reach their terminal velocities.

12. The method of claim 3, comprising varying, scanning or stepping the amplitude of said one or more transient DC voltages or potentials as a function of time during said first mode and/or second mode; and/or wherein said one or more transient DC voltages or potentials have different amplitudes during said first and second modes.

13. The method of claim 12, comprising increasing and/or decreasing the amplitude of said one or more transient DC voltages or potentials as a function of time during said first mode and/or second mode; and/or wherein said one or more transient DC voltages or potentials have a higher amplitude during said first mode than the second mode, or a lower amplitude during said first mode than the second mode.

14. The method of claim 3, wherein the method switches between said first and second modes whilst analysing the same sample in a single experimental run.

15. The method of claim 1, comprising varying, scanning or stepping the velocity of said one or more transient DC voltages or potentials in said first direction as a function of time.

16. The method of claim 15, wherein the ions are separated with higher mass to charge ratio resolution when the one or more transient DC voltages or potentials have a higher velocity, and a lower mass to charge ratio resolution when the one or more transient DC voltages or potentials have a lower velocity.

17. A separation device for separating ions, comprising:
a plurality of electrodes;
a first device arranged and adapted to either (i) apply one or more transient DC voltages or potentials to at least some of said electrodes in order to urge ions in a first direction through said separation device, or (ii) apply multi-phase AC or RF voltages or potentials to at least some of said electrodes and to switch the phase of the voltages or potentials applied to sequential electrodes along the device such that a pseudo-potential barrier moves along the device or to modulate the amplitude of the voltages or potentials in sequence along the device such that a pseudo-potential barrier moves along the device, wherein the potential barrier is configured to urge ions in a first direction through said separation device; and
a second device arranged and adapted to provide a gas flow in a second direction which is substantially inclined or opposed to said first direction; and
a controller arranged and adapted to control the first and second devices so that either (i) the one or more transient DC voltages or potentials, or (ii) the potential barrier, urge the ions against the gas flow such that the ions separate according to their mass to charge ratios.

18. The device of claim 17, wherein the controller is arranged and adapted to control the first and second devices to either:
(i) perform a first mode of operation in which said one or more transient DC voltages are swept, translated or sequentially applied along at least a portion of the axial length of said separation device with a first velocity so as to cause ions to be separated according to their ion mobilities; perform a second mode of operation in which said one or more transient DC voltages are swept, translated or sequentially applied along at least a portion of the axial length of said separation device with a second velocity that is higher than said first velocity so as to cause ions to be separated according to their mass to charge ratios; and provide said gas flow during said first and second modes; or
(ii) perform a first mode of operation in which said one or more AC or RF voltages or potentials are applied along at least a portion of the axial length of said separation device so that said potential barrier moves along the device at a first velocity so as to cause ions to be separated according to their ion mobilities; perform a second mode of operation in which said one or more AC or RF voltages or potentials are applied along at least a portion of the axial length of said separation device so that said potential barrier moves along the device at a second velocity that is higher than said first velocity so as to cause ions to be separated according to their mass to charge ratios; and provide said gas flow during said first and second modes.

19. A mass spectrometer or ion mobility spectrometer comprising a separation device as claimed in claim 17.

20. An ion filter comprising:
a plurality of electrodes;
a first device arranged and adapted to either: (i) apply one or more transient DC voltages or potentials to said electrodes so as to urge the ions in a first direction along the filter, or (ii) apply multi-phase AC or RF voltages or potentials to said electrodes, to switch the phase of the voltages or potentials applied to sequential electrodes along the filter such that a pseudo-potential barrier moves along the filter or modulating the amplitude of the voltages or potentials in sequence along the filter such that a potential barrier moves along the filter, wherein the potential barrier urges the ions in a first direction along the filter;
a second device arranged and adapted to provide a gas flow along the filter in a second direction so as to oppose the motion of the ions in the first direction, wherein the first and second directions are angled with respect to each other at an angle other than being orthogonal; and
a controller arranged and adapted to control the first and second devices so that the one or more transient DC voltages or potentials urge the ions against the gas flow such that ions having different physicochemical property values travel along different paths through the filter and such that only ions of a selected value or range of values of said physicochemical property exit the ion filter along a desired exit path.

* * * * *